United States Patent
Rentsch et al.

(10) Patent No.: US 10,689,520 B2
(45) Date of Patent: Jun. 23, 2020

(54) MODIFIED MINERAL-BASED FILLER COMPRISING COPPER SALTS

(71) Applicant: Omya International AG, Oftringen (CH)

(72) Inventors: Samuel Rentsch, Spiegel bei Bern (CH); Matthias Welker, Hésingue (FR); Simon Urwyler, Bern (CH); Martina Elisabeth Knupfer, Rotkreuz (CH); Joachim Glaubitz, Sins (CH); Patrick A. C. Gane, Rothrist (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 15/564,273

(22) PCT Filed: Apr. 22, 2016

(86) PCT No.: PCT/EP2016/059008
§ 371 (c)(1),
(2) Date: Oct. 4, 2017

(87) PCT Pub. No.: WO2016/173939
PCT Pub. Date: Nov. 3, 2016

(65) Prior Publication Data
US 2018/0134898 A1     May 17, 2018

Related U.S. Application Data

(60) Provisional application No. 62/153,631, filed on Apr. 28, 2015.

(30) Foreign Application Priority Data

Apr. 27, 2015 (EP) ..................... 15165264

(51) Int. Cl.
| | |
|---|---|
| A01N 25/12 | (2006.01) |
| C09C 1/02 | (2006.01) |
| C08K 9/02 | (2006.01) |
| A61Q 19/00 | (2006.01) |
| A61K 8/02 | (2006.01) |
| A61K 8/19 | (2006.01) |
| D21H 19/38 | (2006.01) |
| C09D 5/14 | (2006.01) |
| C09D 7/62 | (2018.01) |
| C04B 20/10 | (2006.01) |
| A01N 25/10 | (2006.01) |
| A01N 25/26 | (2006.01) |
| A01N 59/20 | (2006.01) |
| A61K 8/23 | (2006.01) |
| C08K 3/26 | (2006.01) |
| C08K 3/28 | (2006.01) |
| C08K 3/30 | (2006.01) |

(52) U.S. Cl.
CPC .............. *C09C 1/024* (2013.01); *A01N 25/10* (2013.01); *A01N 25/12* (2013.01); *A01N 25/26* (2013.01); *A01N 59/20* (2013.01); *A61K 8/022* (2013.01); *A61K 8/0241* (2013.01); *A61K 8/19* (2013.01); *A61K 8/23* (2013.01); *A61Q 19/00* (2013.01); *C04B 20/1051* (2013.01); *C04B 20/1055* (2013.01); *C04B 20/1066* (2013.01); *C08K 3/26* (2013.01); *C08K 3/28* (2013.01); *C08K 3/30* (2013.01); *C08K 9/02* (2013.01); *C09C 1/02* (2013.01); *C09D 5/14* (2013.01); *C09D 7/62* (2018.01); *D21H 19/385* (2013.01); *A61K 2800/10* (2013.01); *A61K 2800/412* (2013.01); *A61K 2800/621* (2013.01); *C01P 2004/51* (2013.01); *C01P 2004/61* (2013.01); *C01P 2004/80* (2013.01); *C01P 2006/12* (2013.01); *C01P 2006/22* (2013.01); *C01P 2006/40* (2013.01); *C01P 2006/60* (2013.01); *C01P 2006/62* (2013.01); *C01P 2006/63* (2013.01); *C01P 2006/64* (2013.01); *C01P 2006/82* (2013.01); *C08K 2003/265* (2013.01); *C08K 2003/3045* (2013.01); *C08K 2201/001* (2013.01); *C08K 2201/006* (2013.01)

(58) Field of Classification Search
None
See application file for complete search history.

(56) References Cited

U.S. PATENT DOCUMENTS

| | | |
|---|---|---|
| 2006/0246149 A1 | 11/2006 | Bucholz et al. |
| 2010/0260866 A1 | 10/2010 | Lu |
| 2011/0237726 A1 | 9/2011 | Gane et al. |
| 2013/0137779 A1 | 5/2013 | Wimmer et al. |
| 2013/0338283 A1 | 12/2013 | Gane et al. |
| 2014/0021656 A1 | 1/2014 | Gane et al. |
| 2014/0171545 A1 | 6/2014 | Creasey et al. |

FOREIGN PATENT DOCUMENTS

| | | |
|---|---|---|
| DE | 10042474 A1 | 3/2002 |
| EP | 2159258 A1 | 3/2010 |

(Continued)

OTHER PUBLICATIONS

Zhizhaev et al. "Copper Precipitation from Sulfate Solutions with Calcium Carbonates." ISSN 1070-4272, Russian Journal of Applied Chemistry 2007, vol. 80, No. 10, pp. 1632-1635.

(Continued)

*Primary Examiner* — Jessica Worsham
(74) *Attorney, Agent, or Firm* — Heslin Rothenberg Farley & Mesiti P.C.

(57) ABSTRACT

The present invention relates to a modified mineral-based filler comprising at least one alkaline earth metal carbonate-comprising material, and at least one water insoluble copper salt comprising the copper mineral malachite in an amount of at least 10 wt.-%, which covers at least partially the surface of the at least one alkaline earth metal carbonate-comprising material, and a method of producing the same.

24 Claims, No Drawings

(56) References Cited

FOREIGN PATENT DOCUMENTS

| EP | 2371766 A1 | 10/2011 |
|---|---|---|
| EP | 2377900 A1 | 10/2011 |
| EP | 2390280 A1 | 11/2011 |
| EP | 2390285 A1 | 11/2011 |
| EP | 2447213 A1 | 5/2012 |
| EP | 2524898 A1 | 11/2012 |
| EP | 2722368 A1 | 4/2014 |
| EP | 2770017 A1 | 8/2014 |
| EP | 2840065 A1 | 2/2015 |
| JP | 2000203832 A | 7/2000 |
| WO | 2009058707 A1 | 5/2009 |
| WO | 2010023144 A1 | 3/2010 |
| WO | 2011128242 A1 | 10/2011 |
| WO | 2013142473 A1 | 9/2013 |
| WO | 2014060286 A1 | 4/2014 |
| WO | 2014128087 A1 | 8/2014 |

OTHER PUBLICATIONS

Nassrallah-Aboukais et al. "Stabilization of the Vaterite Structure in the Presence of Copper (II): Thermodynamic and Spectroscopic Studies." Chem. Mater. 1999, 11, 44-51.
International Search Report dated Jun. 22, 2016 for PCT Application No. PCT/EP2016/059008.
Written Opinion of International Searching Authority dated Jun. 22, 2016 for PCT Application No. PCT/EP2016/059008.

MODIFIED MINERAL-BASED FILLER COMPRISING COPPER SALTS

CROSS-REFERENCE TO RELATED APPLICATIONS

This is a U.S. national phase of PCT Application No. PCT/EP2016/059008, filed Apr. 22, 2016, which claims priority to European Application No. 15165264.1, filed Apr. 27, 2015 and U.S. Provisional Application No. 62/153,631, filed Apr. 28, 2015.

The present invention relates to a modified mineral-based filler comprising a water insoluble copper salt, a process for manufacturing the same, and its use.

Almost any article or product of daily life is prone to contamination with microbiological pathogens such as bacteria, viruses, fungi, algae, or yeasts. While a certain amount of microbial contamination may not be critical or can be controlled by cleaning or disinfecting the affected product or following specific hygienic guidelines, there are also many application areas and products in which microbial contaminations may bear a potential health risk or may lead to faster degradation of the infested products. Therefore, it is common practice to treat a lot of products with biocidal compositions or to equip them with preservatives.

Aqueous preparations, for example, and especially suspensions, dispersions or slurries of minerals, fillers or pigments, which are used extensively in the paper, paint, rubber and plastics industries as coatings, fillers, extenders and pigments for papermaking as well as aqueous lacquers and paints are often subject to microbial contamination. Such a contamination can result in changes in the preparation properties such as changes in viscosity and/or pH, discolorations or reductions in other quality parameters, which negatively affect their commercial value. Furthermore, the contaminated filler aqueous preparations may transmit the microorganisms to the later produced product, for example, the plastic or paper product. Therefore, for ensuring an acceptable microbiological quality of aqueous preparations, preservatives or biocides are used over the entire life cycle of the preparation (production, storage, transport, use).

Preservatives are also typically added to pharmaceutical, cosmetic or food products to prevent decomposition by microbial growth or by undesirable chemical changes and to avoid any health hazards. However, many of these preservatives are themselves subject to health concerns, and thus, are increasingly rejected by consumers.

Dry film preservation, meaning preservation of dry products such as coatings and building materials from microbiological degradation to avoid material destruction and visible disfigurement, is also an important and difficult challenge. Preservatives for dry film preservation are typically incorporated in the product and preserve the dry product over a longer period of time by an antimicrobial activity on the dry or wet surface. Such an antimicrobial surface activity is of advantage not only to protect the product itself from degradation or defacement but also to avoid contamination of a surface with pathogenic microorganisms. This is particular useful in the health care sector. However, there is the risk that preservatives are eluted from the dry product over time, for example, due to rain or humid environment, which may pose a danger to human health and the environment.

US 2006/0246149 A1 describes antimicrobial pigments, which are obtainable by agitating a suspension comprising one or more pigments and silver oxide as antimicrobial compound. A modified mineral-based filler with enhanced retention of at least one active ingredient or enhanced antimicrobial capabilities is disclosed in US 2010/0260866. A study concerning copper precipitation from sulphate solutions with calcium carbonate was published by Zhizhaev et al. (Russian Journal of Applied Chemistry 2007, 80(10), 1632-1635).

However, there is still a need in the art for harmless materials with antimicrobial activity, which are suitable for a wide range of applications.

Accordingly, it is an object of the present invention to provide a material which can control microbial contamination but does not represent a hazard to health. It would be desirable that said material is at least partially derivable from natural sources and is not persistent in the environment, but easily biodegradable. It would also be desirable that said material is water-resistant, and thus, can be used in applications subjected to regular water washings. It is also desirable that that the antimicrobial activity of the material can be controlled and can be tailored for a specific application.

It is a further object of the present invention to provide a material which, besides the antimicrobial activity, has additional benefits. For example, it would be desirable that said material can be used as filler material so that it may replace conventionally used fillers in various applications or supplement them. It would also be desirable that such a material confers or enhances the antimicrobial activity of a product, in which it is incorporated, over an extended period without affecting the properties of the product in a negative way. It would also be desirable to provide a material that is suitable for agricultural applications and can release micronutrients to plants. It is a further object of the present invention to provide a material that increases the electrical conductivity of the article wherein it is incorporated.

The foregoing and other objects are solved by the subject-matter as defined herein in the independent claims.

According to one aspect of the present invention, a modified mineral-based filler is provided comprising
  at least one alkaline earth metal carbonate-comprising material, and
  at least one water insoluble copper salt, which covers at least partially the surface of the at least one alkaline earth metal carbonate-comprising material,
  wherein the at least one water insoluble copper salt comprises the copper mineral malachite in an amount of at least 10 wt.-%, based on the total weight of the at least one water insoluble copper salt.

According to a further aspect of the present invention, a process for manufacturing a modified mineral-based filler is provided, comprising the following steps:
  (i) providing at least one alkaline earth metal carbonate-comprising material,
  (ii) providing at least one water soluble copper salt,
  (iii) contacting the at least one alkaline earth metal carbonate-comprising material of step (i), the at least one water soluble copper salt of step (ii), and optionally water, in one or several steps to form a mixture, and
  (iv) heating the mixture obtained from step (iii) to a temperature in the range from 30 to 200° C. to form a modified mineral-based filler.

According to still a further aspect of the present invention, a modified mineral-based filler obtainable by a process according to the present invention is provided.

According to still a further aspect of the present invention, use of a modified mineral-based filler according to the present invention in polymer applications, paper coating applications, paper making, paints, coatings, sealants, printing inks, adhesives, food, feed, pharmaceuticals, concrete, cement, cosmetics, water treatment, engineered wood applications, plasterboard applications, packaging applications and/or agricultural applications is provided, wherein preferably the modified mineral-based filler is a dried modified mineral-based filler.

According to still a further aspect of the present invention, use of a modified mineral-based filler according to the present invention as preservative is provided, wherein preferably the modified mineral-based filler is a dried modified mineral-based filler.

According to still a further aspect of the present invention, use of a modified mineral-based filler according to the present invention for enhancing and/or mediating the antimicrobial activity of a substrate is provided, preferably the antimicrobial activity is against at least one strain of bacteria and/or at least one strain of mould and/or at least one strain of yeast and/or at least one algae, wherein preferably the modified mineral-based filler is a dried modified mineral-based filler.

According to still a further aspect of the present invention, use of a modified mineral-based filler according to the present invention for enhancing the electrical conductivity of a substrate is provided, wherein preferably the modified mineral-based filler is a dried modified mineral-based filler.

According to still a further aspect of the present invention, an article comprising a modified mineral-based filler according to the present invention is provided, wherein the article is selected from paper products, engineered wood products, plasterboard products, polymer products, hygiene products, medical products, healthcare products, filter products, woven materials, nonwoven materials, geotextile products, agriculture products, horticulture products, clothing, footwear products, baggage products, household products, industrial products, packaging products, building products, and construction products.

Advantageous embodiments of the present invention are defined in the corresponding subclaims.

According to one embodiment the modified mineral-based filler is in form of an aqueous suspension. According to another embodiment the modified mineral-based filler is a dried modified mineral-based filler, preferably in powder form, and the moisture content of the modified mineral-based filler is between 0.01 and 5 wt.-%, based on the total weight of the dried modified mineral-based filler.

According to one embodiment the at least one alkaline earth metal carbonate-comprising material has a specific surface area (BET) from 1 to 200 $m^2/g$, as measured using nitrogen and the BET method according to ISO 9277, and/or the total weight of copper on the total surface area of the at least one alkaline earth metal carbonate-comprising material is from 0.001 to 500 $mg/m^2$. According to another embodiment the at least one water insoluble copper salt comprises malachite in an amount of at least 15 wt.-%, preferably at least 20 wt.-%, more preferably at least 25 wt.-%, and most preferably at least 30 wt.-%, based on the total weight of the at least one water insoluble copper salt, and/or the water insoluble copper salt further comprises a copper mineral selected from the group consisting of atacamite, deviline, posnjakite, brochantite, copper oxide, and mixtures thereof, and the total amount of copper minerals including malachite is at least 15 wt.-%, preferably at least 20 wt.-%, more preferably at least 25 wt.-%, and most preferably at least 30 wt.-%, based on the total weight of the at least one water insoluble copper salt.

According to one embodiment the modified mineral-based filler further comprises at least one hydrophobising agent, which covers at least partially the surface of the modified mineral-based filler, wherein the total weight of the at least one hydrophobising agent on the total surface area of the modified mineral-based filler is from 0.001 to 10 $mg/m^2$. According to another embodiment the specific surface area (BET) of the least one alkaline earth metal carbonate-comprising material is from 1 to 150 $m^2/g$, preferably from 2 to 60 $m^2/g$, and more preferably from 2 to 15 $m^2/g$, as measured using nitrogen and the BET method according to ISO 9277, and/or the total weight of copper on the total surface area of the at least one alkaline earth metal carbonate-comprising material is from 0.001 to 300 $mg/m^2$, preferably from 0.1 to 100 $mg/m^2$, and more preferably from 1.5 to 30 $mg/m^2$, and/or the total weight of the at least one hydrophobising agent on the total surface area of the modified mineral-based filler is from 0.001 to 9 $mg/m^2$, preferably from 0.01 to 8 $mg/m^2$, and more preferably from 0.1 to 4 $mg/m^2$.

According to one embodiment the at least one hydrophobising agent is selected from the group consisting of an aliphatic carboxylic acid having a total amount of carbon atoms from $C_4$ to $C_{24}$ and/or reaction products thereof, a mono-substituted succinic anhydride consisting of succinic anhydride mono-substituted with a group selected from a linear, branched, aliphatic and cyclic group having a total amount of carbon atoms from at least $C_2$ to $C_{30}$ in the substituent and/or reaction products thereof, a phosphoric acid ester blend of one or more phosphoric acid mono-ester and/or reaction products thereof and one or more phosphoric acid di-ester and/or reaction products thereof, polyhydrogensiloxane and reaction products thereof, an inert silicone oil, preferably polydimethylsiloxane, and mixtures thereof.

According to one embodiment the process is a batch or a continuous process, preferably a continuous process. According to another embodiment the mixture formed in step (iii) is an aqueous suspension, and the process further comprises a step (v) of separating the modified mineral-based filler from the aqueous suspension after step (iv).

According to one embodiment the process further comprises a step (vi) of drying the modified mineral-based filler after step (iv) or step (v), if present, at a temperature in the range from 60 to 200° C., preferably until the moisture content of the modified mineral-based filler is between 0.01 and 5 wt.-%, based on the total weight of the dried modified mineral-based filler. According to another embodiment the process further comprises a step of treating the modified mineral-based filler obtained in step (iv) during and/or after step (iv) in one or more steps with at least one hydrophobising agent at a temperature from 30 to 200° C., wherein the at least one hydrophobising agent is added in an amount such that the total weight of the at least one hydrophobising agent on the total surface area of the modified mineral-based filler is from 0.001 to 10 $mg/m^2$.

According to one embodiment the at least one water soluble copper salt of step (ii) is provided in form of an aqueous solution or aqueous suspension, preferably the aqueous solution or aqueous suspension comprises carbonate ions, wherein the carbonate ions are derived from a carbonate-comprising compound, which is dissolved in the aqueous solution or aqueous suspension of the at least one water soluble copper salt, or are generated in-situ by treating the aqueous solution or aqueous suspension of the at least one water soluble copper salt with gaseous carbon dioxide. According to another embodiment the at least one alkaline earth metal carbonate-comprising material of step (i) is provided in form of an aqueous suspension, preferably the aqueous suspension comprises carbonate ions, wherein the carbonate ions are at least partially derived from a carbonate-comprising compound, which differs from the at least one alkaline earth metal carbonate-comprising material of step (i) and is dissolved in the aqueous suspension, or are generated in-situ by treating the aqueous suspension of the at least one alkaline earth metal carbonate-comprising material with gaseous carbon dioxide.

According to one embodiment the at least one alkaline earth metal carbonate-comprising material is a calcium carbonate-comprising material, preferably the at least one alkaline earth metal carbonate-comprising material is selected from the group consisting of ground calcium carbonate, preferably marble, limestone and/or chalk, precipitated calcium carbonate, preferably vaterite, calcite and/or aragonite, dolomite, and mixtures thereof, more preferably the at least one alkaline earth metal carbonate-comprising material is selected from the group consisting of dolomitic marble, magnesitic marble, limestone, chalk, and mixtures thereof, and most preferably the at least one alkaline earth metal carbonate-comprising material is ground calcium carbonate. According to another embodiment the at least one water soluble copper salt is selected from the group consisting of copper nitrate, copper sulphate, copper acetate, copper chloride, copper bromide, hydrates thereof, and mixtures thereof, preferably selected from the group consisting of copper sulphate, hydrates thereof, and mixtures thereof. According to still another embodiment the process further comprises a step of grinding and/or fractionating and/or classifying the mixture obtained from step (iii) before, during or after step (iv).

It should be understood that for the purpose of the present invention, the following terms have the following meaning:

An "alkaline earth metal carbonate-comprising material" in the meaning of the present invention can be a mineral material or a synthetic material having a content of alkaline earth metal carbonate of at least 50 wt.-%, preferably 75 wt.-%, more preferably 90 wt.-%, and most preferably 95 wt.-%, based on the total weight of the alkaline earth metal carbonate-comprising material.

The term "dry" or "dried" filler material is understood to be a filler material having less than or equal to 5% by weight of water relative to the filler material weight. The % water (equal to "moisture content") is determined according to the Coulometric Karl Fischer measurement method, wherein the filler material is heated to 220° C., and the water content released as vapour and isolated using a stream of nitrogen gas (at 100 ml/min) is determined in a Coulometric Karl Fischer unit.

"Ground calcium carbonate" (GCC) in the meaning of the present invention is a calcium carbonate obtained from natural sources, such as limestone, marble, or chalk, and processed through a wet and/or dry treatment such as grinding, screening and/or fractionation, for example, by a cyclone or classifier.

"Precipitated calcium carbonate" (PCC) in the meaning of the present invention is a synthesized material, generally obtained by precipitation following a reaction of carbon dioxide and calcium hydroxide (hydrated lime) in an aqueous environment or by precipitation of a calcium- and a carbonate source in water. Additionally, precipitated calcium carbonate can also be the product of introducing calcium- and carbonate salts, calcium chloride and sodium carbonate for example, in an aqueous environment. PCC may have a vateritic, calcitic or aragonitic crystalline form. PCCs are described, for example, in EP 2 447 213 A1, EP 2 524 898 A1, EP 2 371 766 A1, EP 2 840 065 A1, or WO 2013/142473 A1.

Throughout the present document, the "particle size" of an alkaline earth metal carbonate-comprising material, or other particulate material is described by its distribution of particle sizes. The value $d_x$ represents the diameter relative to which x % by weight of the particles have diameters less than $d_x$. This means that the $d_{20}$ value is the particle size at which 20 wt.-% of all particles are smaller, and the $d_{98}$ value is the particle size at which 98 wt.-% of all particles are smaller. The $d_{98}$ value is also designated as "top cut". The $d_{50}$ value is thus the weight median particle size, i.e. 50 wt.-% of all grains are bigger and the remaining 50 wt.-% are smaller than this particle size. For the purpose of the present invention the particle size is specified as weight median particle size $d_{50}$ unless indicated otherwise. For determining the weight median particle size $d_{50}$ value or the top cut particle size $d_{98}$ value a Sedigraph 5100 or 5120 device from the company Micromeritics, USA, can be used. The method and the instrument are known to the skilled person and are commonly used to determine grain size of fillers and pigments. The measurement is carried out in an aqueous solution of 0.1 wt.-% $Na_4P_2O_7$. The samples are dispersed using a high speed stirrer and supersonics.

As used herein the term "polymer" generally includes homopolymers and co-polymers such as, for example, block, graft, random and alternating copolymers, as well as blends and modifications thereof. The polymer can be an amorphous polymer, a crystalline polymer, or a semi-crystalline polymer, i.e. a polymer comprising crystalline and amorphous fractions. The degree of crystallinity is specified in percent and can be determined by differential scanning calorimetry (DSC). An amorphous polymer may be characterized by its glass transition temperature and a crystalline polymer may be characterized by its melting point. A semi-crystalline polymer may be characterized by its glass transition temperature and/or its melting point.

For the purpose of the present invention, the "solids content" of a liquid composition is a measure of the amount of material remaining after all the solvent or water has been evaporated.

A "specific surface area (SSA)" of an alkaline earth metal carbonate-comprising material in the meaning of the present invention is defined as the surface area of the alkaline earth metal carbonate-comprising material divided by its mass. As used herein, the specific surface area is measured by nitrogen gas adsorption using the BET isotherm (ISO 9277:2010) and is specified in $m^2/g$.

For the purpose of the present invention, the term "viscosity" or "Brookfield viscosity" refers to Brookfield viscosity. The Brookfield viscosity is for this purpose measured by a Brookfield DV-III Ultra viscometer at 24° C.±3° C. at 100 rpm using an appropriate spindle of the Brookfield RV-spindle set and is specified in mPa·s. Once the spindle has been inserted into the sample, the measurement is started with a constant rotating speed of 100 rpm. The reported Brookfield viscosity values are the values displayed 60 seconds after the start of the measurement. Based on his technical knowledge, the skilled person will select a spindle from the Brookfield RV-spindle set which is suitable for the viscosity range to be measured. For example, for a viscosity range between 200 and 800 mPa·s the spindle number 3 may be used, for a viscosity range between 400 and 1 600 mPa·s the spindle number 4 may be used, for a viscosity range between 800 and 3 200 mPa·s the spindle number 5 may be used, for a viscosity range between 1 000 and 2 000 000 mPa·s the spindle number 6 may be used, and for a viscosity range between 4 000 and 8 000 000 mPa·s the spindle number 7 may be used.

For the purpose of the present application, "water-insoluble" materials are defined as materials which, when 100 g of said material is mixed with 100 g deionised water and filtered on a filter having a 0.2 μm pore size at 20° C. to recover the liquid filtrate, provide less than or equal to 0.1 g of recovered solid material following evaporation at 95 to 100° C. of 100 g of said liquid filtrate at ambient pressure. "Water-soluble" materials are defined as materials which, when 100 g of said material is mixed with 100 g deionised water and filtered on a filter having a 0.2 μm pore size at 20° C. to recover the liquid filtrate, provide more than 0.1 g of recovered solid material following evaporation at 95 to 100° C. of 100 g of said liquid filtrate at ambient pressure.

A "suspension" or "slurry" in the meaning of the present invention comprises insoluble solids and a solvent or liquid, preferably water, and optionally further additives, and usually contains large amounts of solids and, thus, is more viscous and can be of higher density than the liquid from which it is formed.

A "modified mineral-based filler" in the gist of the present invention comprises at least one alkaline earth metal carbonate-comprising material and at least one water insoluble copper salt. These compounds may be chemically or physically bonded to each other in the wet as well as dry state, which means that no segregation is observed. A blend of at least one alkaline earth metal carbonate-comprising material and at least one water insoluble copper salt, such as malachite, would segregate due to the different density of the compounds, and thus, is not part of present invention.

For the purpose of the present invention, the term "mixture" refers to a combination of at least two substances and includes both a homogeneous and a heterogeneous mixture. The mixture may be in solid or liquid form. For example, a mixture can be in solid form comprising at least one alkaline earth carbonate-comprising material and at least one water soluble copper salt or the mixture can be in liquid form comprising at least one alkaline earth carbonate-comprising material, at least one water soluble copper salt, and water.

"Drying" in the sense of the present invention means that heating is carried out until the moisture content of the modified mineral-based filler is in the range from 0.01 to 5 wt.-%, based on the total weight of the modified mineral-based filler.

"Separating" in the sense of the present invention means that the modified mineral-based filler is removed or isolated from an aqueous suspension by mechanical or thermal methods and the moisture content of the obtained modified mineral-based filler is more than 5 wt.-%, based on the total weight of the modified mineral-based filler.

Where the term "comprising" is used in the present description and claims, it does not exclude other non-specified elements of major or minor functional importance. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Whenever the terms "including" or "having" are used, these terms are meant to be equivalent to "comprising" as defined above.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" even though such a limited understanding is always included by the terms "obtained" or "defined" as a preferred embodiment.

The inventive process for producing a modified mineral-based filler comprises the steps of (i) providing at least one alkaline earth metal carbonate-comprising material, (ii) providing at least one water soluble copper salt, (iii) contacting the at least one alkaline earth metal carbonate-comprising material of step (i), the at least one water soluble copper salt of step (ii), and optionally water, in one or several steps to form a mixture, and (iv) heating the mixture obtained from step (iii) to a temperature in the range from 30 to 200° C. to form a modified mineral-based filler.

In the following details and preferred embodiments of the inventive process will be set out in more details. It is to be understood that these technical details and embodiments also apply to the inventive products and the inventive uses.

The Alkaline Earth Metal Carbonate-Comprising Material

In step (i) of the process of the present invention at least one alkaline earth metal carbonate-comprising material is provided.

According to one embodiment the at least one alkaline earth metal carbonate-comprising material has a content of alkaline earth metal carbonate of at least 50 wt.-%, preferably 75 wt.-%, more preferably 90 wt.-%, and most preferably 95 wt.-%, based on the total weight of the alkaline earth metal carbonate-comprising material. According to another embodiment the at least one alkaline earth metal carbonate comprising material consists of an alkaline earth metal carbonate.

According to one embodiment the alkaline earth metal carbonate is selected from the group consisting of magnesium carbonate, calcium magnesium carbonate, calcium carbonate, or mixtures thereof. Thus, the at least one alkaline earth metal carbonate-comprising material is a magnesium carbonate- and/or a calcium magnesium carbonate- and/or a calcium carbonate-comprising material.

According to one embodiment the at least one alkaline earth metal carbonate-comprising material is a calcium carbonate-comprising material, preferably the at least one alkaline earth metal carbonate-comprising material is selected from the group consisting of ground calcium carbonate, preferably marble, limestone and/or chalk, precipitated calcium carbonate, preferably vaterite, calcite and/or aragonite, dolomite and/or mixtures thereof, more preferably the at least one alkaline earth metal carbonate-comprising material is selected from the group consisting of dolomitic marble, magnesitic marble, limestone, chalk, and mixtures thereof, and most preferably the at least one alkaline earth metal carbonate-comprising material is ground calcium carbonate. According to another embodiment the at least one alkaline earth metal carbonate-comprising material of step i) is calcium carbonate, preferably ground calcium carbonate and/or precipitated calcium carbonate.

Natural or ground calcium carbonate (GCC) is understood to be manufactured from a naturally occurring form of calcium carbonate, mined from sedimentary rocks such as limestone or chalk, or from metamorphic marble rocks, eggshells or seashells. Calcium carbonate is known to exist as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Ground calcium carbonate is almost exclusively of the calcitic polymorph, which is said to be trigonal-rhombohedral and represents the most stable form of the calcium carbonate polymorphs. The term "source" of the calcium carbonate in the meaning of the present application refers to the naturally occurring mineral material from which the calcium carbonate is obtained. The source of the calcium carbonate may comprise further naturally occurring components such as magnesium carbonate, alumino silicate etc.

According to one embodiment of the present invention the source of natural or ground calcium carbonate (GCC) is selected from marble, chalk, limestone, or mixtures thereof. Preferably, the source of ground calcium carbonate is marble, and more preferably dolomitic marble and/or magnesitic marble. According to one embodiment of the present invention the GCC is obtained by dry grinding. According to another embodiment of the present invention the GCC is obtained by wet grinding and subsequent drying.

"Dolomite" in the meaning of the present invention is a calcium carbonate containing mineral, namely a carbonic calcium-magnesium-mineral, having the chemical composition of $CaMg(CO_3)_2$ ("$CaCO_3 \cdot MgCO_3$"). A dolomite mineral may contain at least 30.0 wt.-% $MgCO_3$, based on the total weight of dolomite, preferably more than 35.0 wt.-%, and more preferably more than 40.0 wt.-% $MgCO_3$.

According to one embodiment of the present invention, the calcium carbonate comprises one type of ground calcium carbonate. According to another embodiment of the present invention, the calcium carbonate comprises a mixture of two or more types of ground calcium carbonates selected from different sources.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation by combining calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the calcium carbonate comprises one type of precipitated calcium carbonate. According to another embodiment of the present invention, the calcium carbonate comprises a mixture of two or more precipitated calcium carbonates selected from different crystalline forms and different polymorphs of precipitated calcium carbonate. For example, the at least one precipitated calcium carbonate may comprise one PCC selected from S-PCC and one PCC selected from R-PCC.

According to one embodiment, the at least one alkaline earth metal carbonate-comprising material of step i) is in form of particles having a weight median particle size $d_{50}$ from 0.01 to 100 µm, preferably from 0.1 to 80 µm, more preferably from 0.5 to 50 µm, and most preferably from 1 to 25 µm.

The at least one alkaline earth metal carbonate-comprising material may have a specific surface area (BET) from 1 to 200 m²/g, as measured using nitrogen and the BET method according to ISO 9277. According to one embodiment the specific surface area (BET) of the at least one alkaline earth metal carbonate-comprising material is from 1 to 150 m²/g, preferably from 2 to 60 m²/g, and more preferably from 2 to 15 m²/g, as measured using nitrogen and the BET method according to ISO 9277.

The at least one alkaline earth metal carbonate-comprising material may be used in any suitable liquid or dry form. For example, the at least one alkaline earth metal carbonate-comprising material may be in form of a powder and/or a suspension. The suspension can be obtained by mixing particles of at least one alkaline earth metal carbonate-comprising material with a solvent, preferably water. The at least one alkaline earth metal carbonate-comprising material to be mixed with a solvent, and preferably water, may be provided in any form, for example, as suspension, slurry, dispersion, paste, powder, a moist filter cake or in pressed or granulated form.

The suspension can be undispersed or dispersed, i.e. the suspension includes a dispersant, and thus, forms an aqueous dispersion.

According to one embodiment of the present invention, the at least one alkaline earth metal carbonate-comprising material is used in form of an aqueous suspension, which does not contain a dispersant. According to another embodiment of the present invention, the at least one alkaline earth metal carbonate-comprising material is used in form of an aqueous suspension, which contains a dispersant. A suitable dispersant may be selected from polyphosphates, and is in particular a tripolyphosphate. Another suitable dispersant may be selected from the group comprising homopolymers or copolymers of polycarboxylic acid salts based on, for example, acrylic acid, methacrylic acid, maleic acid, fumaric acid or itaconic acid and acrylamide or mixtures thereof. Homopolymers or copolymers of acrylic acid are especially preferred. The weight average molecular weight $M_w$ of such products is preferably in the range from 2 000 to 15 000 g/mol, with a weight average molecular weight $M_w$ from 3 000 to 7 000 g/mol or 3 500 to 6 000 g/mol being especially preferred. According to an exemplary embodiment, the dispersant is sodium polyacrylate having a weight average molecular weight $M_w$ from 2 000 to 15 000 g/mol, preferably from 3 000 to 7 000 g/mol, and most preferably from 3 500 to 6 000 g/mol.

The solids content of the suspension of the at least one alkaline earth metal carbonate-comprising material can be adjusted by the methods known to the skilled person. To adjust the solids content of an aqueous suspension, for example, the aqueous suspension may be partially dewatered by a settling, filtration, centrifugation or thermal separation process. According to one embodiment of the present invention, the solids content of the aqueous suspension of the at least one alkaline earth metal carbonate-comprising material is from 1 to 85 wt.-%, more preferably from 5 to 75 wt.-%, and most preferably from 10 to 65 wt.-%, based on the total weight of the aqueous suspension. According to another embodiment the solids content of the aqueous suspension of the at least one alkaline earth metal carbonate-comprising material is from 5 to 78 wt.-%, preferably from 10 to 70 wt.-%, and more preferably from 10 to 60 wt.-%, based on the total weight of the aqueous suspension.

According to one embodiment the at least one alkaline earth metal carbonate-comprising material of step (i) is provided in form of an aqueous suspension. The aqueous suspension comprises copper ions, wherein the copper ions are derived from a water soluble copper salt, which is dissolved in the aqueous suspension. The water soluble copper salt may be selected from the water soluble copper salts defined in the following section. According to one embodiment the water soluble copper salt is the same copper salt as provided in step ii) of the inventive process.

According to another embodiment the at least one alkaline earth metal carbonate-comprising material of step (i) is provided in form of an aqueous suspension. According to a preferred embodiment the aqueous suspension comprises carbonate ions, wherein the carbonate ions are at least partially derived from a carbonate-comprising compound, which differs from the at least one alkaline earth metal carbonate-comprising material of step (i) and is dissolved in the aqueous suspension, or are generated in-situ by treating the aqueous suspension of the at least one alkaline earth metal carbonate-comprising material with gaseous carbon dioxide. The carbonate-comprising compound may be selected from the group consisting of sodium carbonate, potassium carbonate, barium carbonate, manganese carbonate and mixtures thereof, preferably sodium carbonate.

According to one embodiment of the present invention, the at least one alkaline earth metal carbonate-comprising material is a calcium carbonate-comprising material, preferably calcium carbonate, and is in form of particles having a weight median particle size $d_{50}$ from 0.01 to 100 µm, preferably from 0.1 to 80 µm, more preferably from 0.5 to 50 µm, and most preferably from 1 to 25 µm, and/or has a specific surface area (BET) from 1 to 200 m$^2$/g, as measured using nitrogen and the BET method according to ISO 9277, preferably from 1 to 150 m$^2$/g, more preferably from 2 to 60 m$^2$/g, and most preferably from 2 to 15 m$^2$/g.

The Water Soluble Copper Salt

In process step (ii) at least one water soluble copper salt is provided. It will be appreciated that the at least one water soluble copper salt is capable of forming a water insoluble salt in the presence of at least one alkaline earth metal carbonate-comprising material. Preferably, the at least one water soluble copper salt may be a water soluble copper(II) salt, i.e. a copper salt, wherein the copper is in oxidation state 2. However, water soluble copper(I) salts or water soluble copper salts in other oxidation states may also be used in the inventive process.

The at least one water soluble copper salt can be an anhydrous salt or a hydrate salt. According to one embodiment, the at least one water soluble copper salt is selected from the group consisting of copper nitrate, copper sulphate, copper acetate, copper chloride, copper bromide, hydrates thereof, and mixtures thereof. According to a preferred embodiment, the at least one water soluble copper salt is selected from the group consisting of copper sulphate and hydrates thereof.

As used herein, a "hydrate" is an inorganic salt containing water molecules combined in a definite ratio as an integral part of the crystal. Depending on the number of water molecules per formula unit of salt, the hydrate may be designated as monohydrate, dihydrate, trihydrate, tetrahydrate, pentahydrate, hexahydrate, heptahydrate, octahydrate, nonahydrate, decahydrate, hemihydrates, etc.

According to one embodiment, the at least one water soluble copper salt is selected from the group consisting of copper nitrate, copper nitrate hexahydrate, copper acetate, copper acetate monohydrate, copper chloride, copper chloride dihydrate, copper sulphate, copper sulphate pentahydrate, and mixtures thereof. However, the at least one water soluble copper salt can also be selected from any other water soluble copper salt known in the art.

According to one embodiment of the present invention, the water soluble copper salt consists of one water soluble copper salt only. Alternatively, the water soluble copper salt can consist of a mixture of two or more water soluble copper salts.

The water soluble copper salt can be provided in form of a solution, a suspension or as a dry material. According to one embodiment, the water soluble copper salt is provided in form of an aqueous solution or aqueous suspension having a copper salt concentration from 1 to 70 wt.-%, based on the total weight of the aqueous solution or aqueous suspension, preferably from 5 to 60 wt.-%, more preferably from 10 to 50 wt.-%, and most preferably from 10 to 45 wt.-%. The concentration of the water soluble copper salt in the aqueous solution or aqueous suspension may also be in the range from 1 to 80 wt.-%, preferably from 5 to 76 wt.-%, more preferably from 10 to 70 wt.-% and most preferably from 10 to 60 wt.-%, based on the total weight of the aqueous solution or aqueous suspension.

According to one embodiment of the present invention, the at least one water soluble copper salt of step ii) is added in an amount from 0.0005 to 25 wt.-%, based on the total weight of the at least one alkaline earth carbonate-comprising material, preferably in an amount from 0.001 to 10 wt.-%, more preferably in an amount from 0.005 to 5 wt.-%, and most preferably in an amount from 0.01 to 3 wt.-%.

According to another embodiment of the present invention, the at least one water soluble copper salt is added in an amount such that the total weight of copper on the surface of the at least one alkaline earth metal carbonate-comprising material is from 0.001 to 500 mg/m$^2$, preferably from 0.001 to 300 mg/m$^2$, more preferably from 0.1 to 100 mg/m$^2$, and most preferably from 1.5 to 30 mg/m$^2$.

According to one embodiment the at least one water soluble copper salt of step (ii) is provided in form of an aqueous solution or an aqueous suspension. According to a preferred embodiment, the aqueous solution or aqueous suspension comprises carbonate ions, wherein the carbonate ions are derived from a carbonate-comprising compound, which is dissolved in the aqueous solution or aqueous suspension of the water soluble copper salt, or are generated in-situ by treating the aqueous solution or aqueous suspension of the at least one water soluble copper salt with gaseous carbon dioxide.

The Inventive Process

According to one aspect of the present invention, a process for manufacturing a modified mineral-based filler is provided comprising the following steps:
(i) providing at least one alkaline earth metal carbonate-comprising material,
(ii) providing at least one water soluble copper salt,
(iii) contacting the at least one alkaline earth metal carbonate-comprising material of step (i), the at least one water soluble copper salt of step (ii), and optionally water, in one or several steps to form a mixture, and
(iv) heating the mixture obtained from step (iii) to a temperature in the range from 30 and 200° C. to form an aqueous suspension of a modified mineral-based filler.

The process of the present invention may be carried out in form of a continuous process or a batch process, preferably in form of a continuous process.

According to one embodiment, the at least one alkaline earth metal carbonate-comprising material provided in step (i) has a temperature from 20 to 200° C., preferably from 50 to 150° C., more preferably from 60 to 130° C., and most preferably from 80 to 120° C. The at least one alkaline earth metal carbonate-comprising material can be provided in solid form or as an aqueous suspension. According to one embodiment of the present invention, the solids content of the aqueous suspension of the at least one alkaline earth metal carbonate-comprising material is from 1 to 85 wt.-%, more preferably from 5 to 75 wt.-%, and most preferably from 10 to 65 wt.-%, based on the total weight of the aqueous suspension. According to another embodiment the solids content of the aqueous suspension of the at least one alkaline earth metal carbonate-comprising material is from 5 to 78 wt.-%, preferably from 10 to 70 wt. %, and more preferably from 10 to 60 wt.-%, based on the total weight of the aqueous suspension.

According to another embodiment the at least one alkaline earth metal carbonate-comprising material provided in step (i) is precipitated calcium carbonate generated from milk of lime and carbon dioxide, and the copper salt provided in step (ii) is provided during or after the precipitation of the calcium carbonate, preferably the copper salt as provided in step (ii) is copper sulphate or a hydrate thereof.

According to one embodiment, the at least one water soluble copper salt provided in step (ii) has a temperature from 20 to 200° C., preferably from 50 to 150° C., more preferably from 60 to 130° C., and most preferably from 80 to 120° C.

According to one embodiment, the at least one water soluble copper salt is provided in form of an aqueous solution or aqueous suspension. The aqueous solution or aqueous suspension may have a temperature from 1 to 95° C., preferably from 10 to 80° C., more preferably from 15 to 50° C., and most preferably from 20 to 30° C. The concentration of the water soluble copper salt in the aqueous solution or aqueous suspension may be in the range from 1 to 80 wt %, preferably from 5 to 76 wt.-%, more preferably from 10 to 70 wt.-% and most preferably from 10 to 60 wt.-%, based on the total weight of the aqueous solution or aqueous suspension. According to one embodiment, the water soluble copper salt is provided in form of an aqueous solution or aqueous suspension having a copper salt concentration from 1 to 70 wt.-%, based on the total weight of the aqueous solution or aqueous suspension, preferably from 5 to 60 wt.-%, more preferably from 10 to 50 wt.-%, and most preferably from 10 to 45 wt.-%.

According to step (iii) of the inventive process, the at least one alkaline earth metal carbonate-comprising material of step (i), the at least one water soluble copper salt of step (ii) and water are contacted in one or several steps to form a mixture.

According to one embodiment of the present invention, step (iii) comprises the steps of contacting the at least one alkaline earth metal carbonate-comprising material of step (i) and the at least one water soluble copper salt of step (ii) in a first step, and subsequently adding water. According to another embodiment of the present invention, step (iii) comprises the steps of contacting the at least one alkaline earth metal carbonate-comprising material of step (i) and water in a first step, and subsequently adding the at least one water soluble copper salt of step (ii). According to still another embodiment of the present invention, step (iii) comprises the steps of contacting the at least one water soluble copper salt of step (ii) and water in a first step, and subsequently adding the at least one alkaline earth metal carbonate-comprising material of step (i).

According to one embodiment of the present invention, step (iii) comprises the steps of providing the at least one alkaline earth metal carbonate-comprising material of step (i) in a first step, and subsequently adding the at least one water soluble copper salt of step (ii) and water. The at least one water soluble copper salt and water may be added together in form of an aqueous solution or an aqueous suspension of the at least one water soluble copper salt. According to another embodiment of the present invention, step (iii) comprises the steps of providing the at least one water soluble copper salt of step (ii) in a first step, and subsequently adding the at least one alkaline earth metal carbonate-comprising material of step (i) and water. The at least one alkaline earth metal carbonate-comprising material and water may be added together in form of an aqueous suspension of the at least one alkaline earth metal carbonate-comprising material. According to still another embodiment, the at least one alkaline earth metal carbonate-comprising material of step (i), the at least one water soluble copper salt of step (ii) and water are contacted simultaneously.

According to another embodiment, step (iii) consist of contacting the at least one alkaline earth metal carbonate-comprising material of step (i) and at least one water soluble copper salt of step (ii).

The contacting step (iii) can be carried out by any means known in the art. For example, the at least one alkaline earth metal carbonate-comprising material of step (i), the at least one water soluble copper salt of step (ii) and water can be brought into contact by spraying and/or mixing. Suitable process equipment for spraying or mixing is known to the skilled person.

According to one embodiment of the present invention, process step (iii) is carried out by spraying. According to another embodiment of the present invention, process step (iii) is carried out by mixing. The skilled person will adapt the mixing conditions such as the mixing speed and temperature according to his process equipment.

Process step (iii) may be carried out at room temperature, i.e. at a temperature of 20° C.±2° C., or at other temperatures. According to one embodiment, step (iii) is performed at a temperature from 20 to 200° C., preferably from 50 to 150° C., more preferably from 60 to 130° C., and most preferably from 80 to 120° C.

Depending on the amount of water that is introduced during step (iii) by contacting the aforementioned compounds, the mixture may be obtained in suspension, a wet or moist solid material. It is also possible to carry out step (iii) without adding water and providing the materials in steps (i) and (ii) in a dry state. It is also within the confines of the present invention that additional water may be introduced during process step (iii), for example, in order to control and/or maintain and/or achieve the desired solids content or Brookfield viscosity of the obtained mixture. According to one embodiment the solids content of the mixture obtained in step (iii) is from 5 to 80 wt.-%, preferably from 20 to 78 wt.-%, based on the total weight of the mixture. The Brookfield viscosity of the obtained mixture may be from 10 to 10 000 mPa·s, preferably from 50 to 1 000 mPa·s.

In step (iv) of the process of the present invention, the mixture of step (iii) is heated to a temperature in the range from 30 to 200° C. to form a modified mineral-based filler. According to one embodiment, in step (iv) the mixture of step (iii) is heated to a temperature in the range from 70 to 140° C., preferably from 80 to 130° C., and more preferably from 90 to 120° C. The temperature of steps (iii) and step (iv) may be the same or different. According to a preferred embodiment, the temperature of steps (iii) and step (iv) is the same. In the gist of the present invention heating means keeping the mixture obtained from step (iii) at a temperature in the range from 30 to 200° C., or one of the preferred temperature ranges, for a finite period of time. The term "heating" is not limiting the process according to the present invention to a process, wherein the temperature of the mixture is adjusted to the temperature range of 30 to 200° C. by addition of energy through an external heat source during step (iv), but also comprises keeping a preheated mixture, which is obtained by e.g. providing a preheated at least one alkaline earth metal carbonate-comprising material of step (i) and/or a preheated at least one water soluble copper salt of step (ii), or preheating the mixture during step (iii). For the sake of completeness, it should be mentioned here that in case the temperature of the mixture obtained from step (iv) is higher than 200° C., adjusting the temperature to a range from 30 to 200° C. is also covered by the term heating. According to one embodiment of the present invention, in step (iv) of the process of the present invention, the mixture of step (iii) is adjusted to a temperature in the range from 30 to 200° C. to form a modified mineral-based filler.

In case the process of the present invention is carried out in form of a continuous process, the heating step may be carried out for 3 milliseconds to 60 seconds, and preferably for 10 milliseconds to 30 seconds. In case that the process of the present invention is carried out in form of a batch process, the heating step may be carried out for 1 to 180 minutes, preferably 3 to 130 minutes, and more preferably from 5 to 30 minutes.

The skilled person will appreciate that step (iv) is carried out for a time period sufficient to form a modified mineral-based filler. According to one embodiment of the present invention, process step (iv) is carried out for at least 1 min, preferably for at least 5 min. According to one embodiment, process step (iv) is carried out by heating the mixture to a temperature in the range from 30 to 200° C. for at least 10 min, preferably at least 20 min, more preferably at least 1 h, even more preferably for at least 2 h, and most preferably for at least 3 h.

According to one embodiment, the heating step (iv) is carried out until 30 to 99.8 mol-%, preferably 60 to 95 mol-% of the at least one water soluble copper salt provided in step (ii) is precipitated in form of an water insoluble copper salt on at least a part of the surface of the at least one alkaline earth metal carbonate-comprising material to form a modified mineral-based filler. It is believed that the precipitation of the insoluble copper salt follows the Arrhenius equation, which means that increasing of the temperature allows to shorten the reaction time and decreasing the temperatures leads to a prolonged reaction time.

The heating step (iv) can be carried out at reduced pressure, ambient pressure or under increased pressure. For temperatures above 100° C. it is preferred to carry out the heating step under increased pressure.

It is also within the confines of the present invention that process step (iii) and process step (iv) can be carried out simultaneously. Thus, the step of contacting of the at least one alkaline earth metal carbonate-comprising material of step (i), the at least one water soluble copper salt of step (ii), and optionally water, and the step of heating the mixture to a temperature in the range from 30 and 200° C. may be carried out simultaneously.

By means of step (iv), a modified mineral-based filler is obtained. According to one embodiment the modified mineral-based filler is obtained in form of an aqueous suspension. The aqueous suspension may have a solid content in the range from 1 to 80 wt.-%, more preferably in the range from 10 to 78 wt.-%, and most preferably in the range from 20 to 50 wt.-%, based on the weight of the modified mineral-based filler in the suspension. If necessary, additional water may be introduced during process step (iv), for example, in order to control and/or maintain and/or achieve the desired solids content or Brookfield viscosity of the obtained aqueous suspension.

According to one embodiment of the present invention, a process for manufacturing a modified mineral-based filler is provided comprising the following steps:
  (i) providing at least one calcium carbonate-comprising material, preferably calcium carbonate,
  (ii) providing at least one water soluble copper salt, preferably in form of an aqueous solution or an aqueous suspension, wherein the at least one water soluble copper salt is selected from the group consisting of copper nitrate, copper sulphate, copper acetate, copper chloride, copper bromide, hydrates thereof, and mixtures thereof, preferably selected from the group consisting of copper sulphate, hydrates thereof, and mixtures thereof,
  (iii) contacting the at least one calcium carbonate-comprising material of step (i), the at least one water soluble copper salt of step (ii), and optionally water, in one or several steps to form a mixture, and
  (iv) heating the mixture obtained from step (iii) to a temperature in the range from 30 and 200° C. to form a modified mineral-based filler.

According to a further preferred embodiment, in step (iii) the at least one alkaline earth metal carbonate-comprising material of step (i) is provided in a first step, and subsequently the at least one water soluble copper salt and water are added.

Additional Process Steps

According to one embodiment, the process of the present invention further comprises a step of grinding and/or fractionating and/or classifying the mixture obtained from step (iii) before, during or after step (iv). According to another embodiment, the process further comprises a step of filtrating the mixture obtained from step (iii) before step (iv). According to still another embodiment, the process further comprises the steps of grinding and/or fractionating and/or classifying the mixture obtained from step (iii), and subsequently, filtrating the obtained ground mixture before step (iv).

The grinding step may be undertaken by all the techniques and grinders well known to the man skilled in the art for wet grinding. The grinding step may be carried out with a conventional grinding device, for example, under conditions such that refinement predominantly results from impacts with a secondary body, i.e. in one or more of: a ball mill, a rod mill, a vibrating mill, a centrifugal impact mill, a vertical bead mill, an attrition mill, or other such equipment known to the skilled person. The grinding step may be carried out in batch or continuously, preferably continuously. Preferably the grinding step may be carried out without adding compounds different from the compounds as provided in steps (i) and (ii).

The mixture obtained from step (iii) may be filtrated in order to remove salts or water.

The obtained modified mineral-based filler may be further processed, e.g., in case the modified mineral-based filler is obtained in form of a suspension, the modified mineral-based filler may be separated from the aqueous suspension and/or subjected to a surface treatment step and/or a drying step.

According to one embodiment of the present invention, the mixture formed in step (iii) of the inventive process is an aqueous suspension and the process further comprises a step (v) of separating the modified mineral-based filler from the aqueous suspension after step (iv). Thus, a process for manufacturing a modified mineral-based filler may comprise the following steps:
(i) providing at least one alkaline earth metal carbonate-comprising material,
(ii) providing at least one water soluble copper salt,
(iii) contacting the at least one alkaline earth metal carbonate-comprising material of step (i), the at least one water soluble copper salt of step (ii), and optionally water, in one or several steps to form a mixture in form of an aqueous suspension,
(iv) heating the mixture obtained from step (iii) to a temperature in the range from 30 and 200° C. to form an aqueous suspension of modified mineral-based filler, and
(v) separating the modified mineral-based filler from the aqueous suspension obtained from step (iv).

The modified mineral-based filler obtained from step (iv) may be separated from the aqueous suspension by any conventional means of separation known to the skilled person. According to one embodiment of the present invention, in process step (v) the modified mineral-based filler is separated mechanically and/or thermally. Examples of mechanical separation processes are filtration, e.g. by means of a drum filter or filter press, nanofiltration, or centrifugation. An example for a thermal separation process is a concentrating process by the application of heat, for example, in an evaporator. According to a preferred embodiment, in process step (v) the modified mineral-based filler is separated mechanically, preferably by filtration and/or centrifugation.

According to one embodiment of the present invention, the process further comprises a step of washing the modified mineral-based filler obtained from step (v) with water. The modified mineral-based filler may be washed with water and/or a suitable solvent, preferably water. Suitable solvents are known in the art and are, for example, aliphatic alcohols, ethers and diethers having from 4 to 14 carbon atoms, glycols, alkoxylated glycols, glycol ethers, alkoxylated aromatic alcohols, aromatic alcohols, mixtures thereof, or mixtures thereof with water. For example, the modified mineral-based filler can be washed one time, two times or three times with water and/or a suitable solvent, preferably water.

After separation, the modified mineral-based filler can be dried in order to obtain a dried modified mineral-based filler. According to one embodiment the process of the present invention further comprises a step (vi) of drying the modified mineral-based filler after step (iv) or step (v), if present, at a temperature in the range from 60 to 200° C., preferably until the moisture content of the modified mineral-based filler is between 0.01 and 5 wt.-%, based on the total weight of the dried modified mineral-based filler.

According to one embodiment of the present invention, a process for manufacturing a dried modified mineral-based filler is provided comprising the following steps:
(i) providing at least one alkaline earth metal carbonate-comprising material,
(ii) providing at least one water soluble copper salt,
(iii) contacting the at least one alkaline earth metal carbonate-comprising material of step (i), the at least one water soluble copper salt of step (ii) and water in one or several steps to form a mixture,
(iv) heating the mixture obtained from step (iii) to a temperature in the range from 30 and 200° C. to form an aqueous suspension of modified mineral-based filler,
(v) separating the modified mineral-based filler from the aqueous suspension obtained from step (iv), and
(vi) drying the modified mineral-based filler.

In general, the drying step (vi) may take place using any suitable drying equipment and can, for example, include thermal drying and/or drying at reduced pressure using equipment such as an evaporator, a flash drier, an oven, a spray drier and/or drying in a vacuum chamber. The drying step (vi) can be carried out at reduced pressure, ambient pressure or under increased pressure. For temperatures below 100° C. it may be preferred to carry out the drying step under reduced pressure.

According to one preferred embodiment, the separation is carried out by a thermal method. This may allow to dry the modified mineral-based filler subsequently without changing the equipment.

According to one embodiment, in process step (vi) the modified mineral-based filler is dried until the moisture content of the formed modified mineral-based filler is less than or equal to 1.0 wt.-%, based on the total weight of the dried modified mineral-based filler, preferably less than or equal to 0.5 wt.-%, and more preferably less than or equal to 0.2 wt.-%. According to another embodiment, in process step (vi) the modified mineral-based filler is dried until the moisture content of the formed modified mineral-based filler is between 0.01 and 0.15 wt.-%, preferably between 0.02 and 0.10 wt.-%, and more preferably between 0.03 and 0.07 wt.-%, based on the total weight of the dried modified mineral-based filler.

According to a further aspect of the present invention, a modified mineral-based filler is provided, obtainable by a process according to present invention. Accordingly, the modified mineral-based filler may be obtainable by the following steps:
(i) providing at least one alkaline earth metal carbonate-comprising material, (ii) providing at least one water soluble copper salt,
(iii) contacting the at least one alkaline earth metal carbonate-comprising material of step (i), the at least one water soluble copper salt of step (ii), and optionally water, in one or several steps to form a mixture, and
(iv) heating the mixture obtained from step (iii) to a temperature in the range from 30 and 200° C. to form a modified mineral-based filler,
(v) optionally separating the modified mineral-based filler from the aqueous suspension obtained from step (iv), and
(vi) optionally drying the modified mineral-based filler at a temperature range from 60 t 200° C. until the moisture content of the modified mineral-based filler is between 0.01 and 5 wt.-%, based on the total weight of the dried modified mineral-based filler.

Additional Surface Treatment

The modified mineral-based filler formed in step (iv) of the inventive process can be post-treated, preferably after steps (v) or (vi), if present. However, it may also be possible to carry out the surface treatment on a wet product. According to one embodiment the modified mineral-based filler is treated with a fatty acid, e.g. stearic acid, a silane, or phosphoric esters of fatty acids, or a siloxane.

According to one embodiment the process of the present invention further comprises a step of treating the modified mineral-based filler formed in step (iv) during and/or after step (iv) in one or more steps with at least one hydrophobising agent, preferably at a temperature from 30 to 200° C. Preferably, the surface treatment is carried out on the dried modified mineral-based filler. Thus, according to one embodiment of the present invention, the inventive process comprises a step (vi) of drying the modified mineral-based filler after step (iv) or after step (v), if present, and the dried modified mineral-based filler is treated after drying step (vi) in one or more steps with at least one hydrophobising agent, preferably at a temperature from 30 to 200° C. According to one embodiment the modified mineral-based filler formed in step (iv) is treated during and/or after step (iv) in one or more steps with at least one hydrophobising agent at a temperature from 30 to 200° C., preferably from 60 to 130° C., more preferably from 70 to 120° C., and most preferably from 80 to 110° C.

According to one embodiment the at least one hydrophobising agent is added in an amount such that the total weight of the at least one hydrophobising agent on the total surface area of the alkaline earth metal carbonate-comprising material is from 0.001 to 10 mg/m$^2$ preferably from 0.001 to 9 mg/m$^2$, more preferably from 0.01 to 8 mg/m$^2$, and most preferably from 0.1 to 4 mg/m$^2$.

According to one embodiment of the present invention, the process further comprises a step of treating the modified mineral-based filler formed in step (iv) during and/or after step (iv) in one or more steps with at least one hydrophobising agent at a temperature from 30 to 200° C., wherein the hydrophobising agent is added in an amount such that the total weight of the at least one hydrophobising agent on the total surface area of the alkaline earth metal carbonate-comprising material is from 0.001 to 10 mg/m$^2$.

Suitable hydrophobising agents are, for example, fatty acids, aliphatic carboxylic acids, aliphatic carboxylic esters, mono-substituted succinic anhydrides, mono-substituted succinic acids, or phosphoric acid esters. Suitable hydrophobising agents and methods for preparing surface-treated filler products thereof are, for example, described in EP 2 159 258 A1, EP 2 390 285 A1, EP 2 390 280 A1, WO 2014/060286 A1 and WO 2014/128087 A1.

In one embodiment, the hydrophobising agent is an aliphatic carboxylic acid having a total amount of carbon atoms from $C_4$ to $C_{24}$ and/or reaction products thereof.

The term "reaction products" of the aliphatic carboxylic acid in the meaning of the present invention refers to products obtained by contacting the modified mineral-based filler with the at least one aliphatic carboxylic acid. Said reaction products are formed between at least a part of the at least one aliphatic carboxylic acid and reactive molecules located at the surface of the alkaline earth metal carbonate-comprising material particles.

The aliphatic carboxylic acid in the meaning of the present invention may be selected from one or more straight chain, branched chain, saturated, unsaturated and/or alicyclic carboxylic acids. Preferably, the aliphatic carboxylic acid is a monocarboxylic acid, i.e. the aliphatic carboxylic acid is characterized in that a single carboxyl group is present. Said carboxyl group is placed at the end of the carbon skeleton.

In one embodiment of the present invention, the aliphatic carboxylic acid is selected from saturated unbranched carboxylic acids, that is to say the aliphatic carboxylic acid is preferably selected from the group of carboxylic acids consisting of pentanoic acid, hexanoic acid, heptanoic acid, octanoic acid, nonanoic acid, decanoic acid, undecanoic acid, lauric acid, tridecanoic acid, myristic acid, pentadecanoic acid, palmitic acid, heptadecanoic acid, stearic acid, nonadecanoic acid, arachidic acid, heneicosylic acid, behenic acid, tricosylic acid, lignoceric acid and mixtures thereof.

In another embodiment of the present invention, the aliphatic carboxylic acid is selected from the group consisting of octanoic acid, decanoic acid, lauric acid, myristic acid, palmitic acid, stearic acid, arachidic acid and mixtures thereof. Preferably, the aliphatic carboxylic acid is selected from the group consisting of myristic acid, palmitic acid, stearic acid and mixtures thereof. For example, the aliphatic carboxylic acid is stearic acid.

Additionally or alternatively, the hydrophobising agent can be at least one mono-substituted succinic acid and/or salty reaction product(s) and/or at least one phosphoric acid ester blend of one or more phosphoric acid mono-ester and/or reaction products thereof and one or more phosphoric acid di-ester and/or reaction products thereof. Methods for treating a calcium carbonate-comprising material with these hydrophobising agents are described, for example, in EP 2 722 368 A1 and EP 2 770 017 A1.

According to one embodiment, the at least one hydrophobising agent is selected from the group consisting of an aliphatic carboxylic acid having a total amount of carbon atoms from $C_4$ to $C_{24}$ and/or reaction products thereof, a mono-substituted succinic anhydride consisting of succinic anhydride mono-substituted with a group selected from a linear, branched, aliphatic and cyclic group having a total amount of carbon atoms from at least $C_2$ to $C_{30}$ in the substituent and/or reaction products thereof, a phosphoric acid ester blend of one or more phosphoric acid mono-ester and/or reaction products thereof and one or more phosphoric acid di-ester and/or reaction products thereof, polyhydrogensiloxane and reaction products thereof, an inert silicone oil, preferably polydimethylsiloxane, and mixtures thereof.

The term "succinic anhydride", also called dihydro-2,5-furandione, succinic acid anhydride or succinyl oxide, has the molecular formula $C_4H_4O_3$ and is the acid anhydride of succinic acid. The term "mono-substituted succinic anhydride" in the meaning of the present invention refers to a succinic anhydride wherein a hydrogen atom is substituted by another substituent.

The term "reaction products of at least one mono-substituted succinic anhydride" in the meaning of the present invention refers to products obtained by contacting a alkaline earth metal carbonate-comprising material with one or more mono-substituted succinic anhydride(s). Said salty reaction products are formed between the mono-substituted succinic acid which is formed from the applied mono-substituted succinic anhydride and reactive molecules located at the surface of the alkaline earth metal carbonate-comprising material.

The term "phosphoric acid mono-ester" in the meaning of the present invention refers to an o-phosphoric acid molecule mono-esterified with one alcohol molecule selected from unsaturated or saturated, branched or linear, aliphatic or aromatic alcohols having a total amount of carbon atoms from $C_6$ to $C_{30}$, preferably from $C_8$ to $C_{22}$, more preferably from $C_8$ to $C_{20}$, and most preferably from $C_8$ to $C_{18}$ in the alcohol substituent. The term "phosphoric acid di-ester" in the meaning of the present invention refers to an o-phosphoric acid molecule di-esterified with two alcohol molecules selected from the same or different, unsaturated or saturated, branched or linear, aliphatic or aromatic alcohols having a total amount of carbon atoms from $C_6$ to $C_{30}$, preferably from $C_8$ to $C_{22}$, more preferably from $C_8$ to $C_{20}$, and most preferably from $C_8$ to $C_{18}$ in the alcohol substituent.

The term "salty reaction products of a phosphoric acid ester or blend of one or more phosphoric acid mono-esters and/or one or more phosphoric acid di-esters" in the meaning of the present invention refers to products obtained by contacting an alkaline earth metal carbonate-comprising material with one or more phosphoric acid mono-ester and one or more phosphoric acid di-ester and optionally phosphoric acid. Said salty reaction products are formed between the applied one or more phosphoric acid mono-ester and one or more phosphoric acid di-ester and optionally phosphoric acid and reactive molecules located at the surface of the alkaline earth metal carbonate-comprising material.

The Modified Mineral-Based Filler

According to one aspect of the present invention, a modified mineral-based filler is provided, comprising
- at least one alkaline earth metal carbonate-comprising material, and
- at least one water insoluble copper salt, which covers at least partially the surface of the at least one alkaline earth metal carbonate-comprising material,
- wherein the at least one water insoluble copper salt comprises the copper mineral malachite in an amount of at least 10 wt.-%, based on the total weight of the at least one water insoluble copper salt.

According to one embodiment, the modified mineral-based filler is in form of particles having a weight median particle size $d_{50}$ from 0.01 to 100 μm, preferably from 0.1 to 80 μm, more preferably from 0.5 to 50 μm, and most preferably from 1 to 25 μm.

The modified mineral-based filler of the present invention can be provided in form of a suspension of modified mineral-based filler, as a separated modified mineral-based filler or as a dried modified mineral-based filler. According to a preferred embodiment the modified mineral-based filler is a dried modified mineral-based filler.

In case the modified mineral-based filler has been dried, the moisture content of the dried modified mineral-based filler can be between 0.01 and 5 wt.-%, based on the total weight of the dried modified mineral-based filler. According to one embodiment, the moisture content of the dried modified mineral-based filler is less than or equal to 1.0 wt.-%, based on the total weight of the dried modified mineral-based filler, preferably less than or equal to 0.5 wt.-%, and more preferably less than or equal to 0.2 wt.-%. According to another embodiment, the moisture content of the dried modified mineral-based filler is between 0.01 and 0.15 wt.-%, preferably between 0.02 and 0.10 wt.-%, and more preferably between 0.03 and 0.07 wt.-%, based on the total weight of the dried modified mineral-based filler.

The following paragraphs are intended to refer to the aqueous suspension of modified mineral-based filler, the separated modified mineral-based filler as well as the dried mineral-based filler.

The inventors surprisingly found that by the inventive process a modified mineral-based filler is formed, which comprises at least one alkaline earth metal carbonate-comprising material and at least one water insoluble copper salt comprising the copper mineral malachite, which covers at least partially the surface of the at least one alkaline earth metal carbonate-comprising material. It is believed that by contacting alkaline earth metal carbonate-comprising material particles with a water soluble copper salt, a water insoluble copper salt can be formed, which may precipitate at least partially on the surface of the particles. It was also found that the water insoluble copper salts formed on at least a part of the surface of the alkaline earth metal carbonate-comprising material may comprise other water insoluble copper minerals than malachite, such as atacamite, deviline, posnjakite, brochantite, or copper oxide. These naturally occurring minerals are well known and may be less harmful to the environment. The use of malachite in agricultural applications, for example, is admitted and regulated by law.

Furthermore, the inventors of the present invention found that the modified mineral-based fillers may exhibit antimicrobial activity in dry products or wet products, preferably dry products. Therefore, the inventive fillers can be used in suspensions, dispersions or slurries of minerals, fillers or pigments, which are typically employed in the paper, paint, rubber and plastics industries as coatings, fillers, extenders and pigments for papermaking as well as aqueous lacquers and paints intended for the preparation of dry or wet products, wherein the dry products are preferred. The inventive fillers may also substitute conventional fillers completely or partially. Since both the alkaline earth metal carbonate-comprising material and the surface-layer of water insoluble copper salt are resistant to water, a long lasting antimicrobial effect can be provided by the inventive modified mineral-based filler. Thus, the inventive filler can even be used in articles, which involve contact with water or subjected regularly to water washing, such as paints or cloths. A further advantage is that, depending on the amount of water insoluble salts on the surface of the alkaline earth metal carbonate-comprising material, the modified mineral-based filler can have a white colour, which may be especially suitable for applications such as paper production.

Moreover, it was found that the inventive modified mineral-based filler may release minor amounts of copper ions, and thus, may be used as micronutrient delivery agent and plant protection product on the same time. For example, the inventive filler may be used to replace conventional plant protection products such as the Bordeaux mixture used in vineyard treatments.

According to one embodiment the at least one alkaline earth metal carbonate-comprising material has a specific surface area (BET) from 1 to 200 $m^2$/g, as measured using nitrogen and the BET method according to ISO 9277, and/or the total weight of copper on the total surface area of the at least one alkaline earth metal carbonate-comprising material is from 0.001 to 500 mg/$m^2$. Means and methods to determine the total weight of copper on the total surface area of the at least one alkaline earth metal carbonate-comprising material are known to the skilled person. For example, the total weight of copper on the total surface area of the at least one alkaline earth metal carbonate-comprising material can be determined by X-ray fluorescence analysis, atomic emission spectroscopy, gravimetric analysis or volumetric analysis.

The BET surface of the modified mineral-based filler may be the same as the BET surface of the alkaline earth metal carbonate-comprising material provided in step (i). The at least one alkaline earth metal carbonate-comprising material may have a specific surface area (BET) from 1 to 200 $m^2$/g, as measured using nitrogen and the BET method according to ISO 9277. According to one embodiment the specific surface area (BET) of the modified mineral-based filler is from 1 to 200 $m^2$/g, preferably from 1 to 150 $m^2$/g, more preferably from 2 to 60 $m^2$/g, and most preferably from 2 to 15 $m^2$/g, as measured using nitrogen and the BET method according to ISO 9277.

According to one embodiment of the present invention, the modified mineral-based filler comprises at least one water insoluble copper salt, which covers at least partially the surface of the at least one alkaline earth metal carbonate-comprising material, the at least one water insoluble copper salt comprises the copper mineral malachite in an amount of at least 15 wt.-%, preferably at least 20 wt.-%, more preferably at least 25 wt.-%, and most preferably at least 30 wt.-%, based on the total weight of the at least one water insoluble copper salt, and/or the water insoluble copper salt further comprises a copper mineral selected from the group consisting of atacamite, deviline, posnjakite, brochantite, copper oxide, and/or mixtures thereof, and the total amount of these copper minerals including malachite is at least 15 wt.-%, preferably at least 20 wt.-%, more preferably at least 25 wt.-%, and most preferably at least 30 wt.-%, based on the total weight of the at least one water insoluble copper salt. According to a preferred embodiment the amount of brochantite is smaller than 30 wt.-%, preferably smaller than 20 wt.-%, more preferably smaller 10 wt.-%, and even more preferably smaller than 5 wt.-%, based on the total weight of the at least one water insoluble copper salt. The amount of the copper salt can be determined by any method known in the art. For example, copper salt can be quantified by inductively coupled plasma mass spectroscopy (ICP-MS) as described in the experimental section. The identification of the copper mineral can be done by X-ray powder diffraction.

According to one embodiment of the present invention, the water insoluble copper salt covers at least 10% of the total surface area of the at least one alkaline earth metal carbonate-comprising material. According to another embodiment, the water insoluble copper salt covers at least 25%, preferably at least 50%, more preferably at least 75%, and most preferably at least 95% of the total surface area of the at least one alkaline earth metal carbonate-comprising material. According to still another embodiment the water insoluble copper salt covers the surface of the at least one alkaline earth metal carbonate-comprising material completely, i.e. 100% of the total surface area of the at least one alkaline earth metal carbonate-comprising material is covered.

The modified mineral-based filler may also comprise at least one hydrophobising agent, which covers at least partially the surface of the modified mineral-based filler. Said hydrophobising agent may render the modified mineral-based filler more compatible for polymer or paint applications.

According to one embodiment of the present invention, the at least one hydrophobising agent covers at least 10% of the total surface area of the modified mineral-based filler. According to another embodiment, the at least one hydrophobising agent covers at least 25%, preferably at least 50%, more preferably at least 75%, and most preferably at least 95% of the total surface area of modified mineral-based filler. According to still another embodiment the at least one hydrophobising agent covers the surface of the modified mineral-based filler completely, i.e. 100% of the total surface area of the modified mineral-based filler is covered.

According to one embodiment of the present invention, the modified mineral-based filler comprises at least one hydrophobising agent, wherein the total weight of the at least one hydrophobising agent on the total surface area of the alkaline earth metal carbonate-comprising material is from 0.001 to 10 mg/m$^2$. Means and methods to determine the total weight of the at least one hydrophobising agent on the total surface area of the at least one alkaline earth metal carbonate-comprising material are known to the skilled person. The total weight of the at least one hydrophobising agent on the total surface area of the at least one alkaline earth metal carbonate-comprising material can be determined, for example, by thermographimetric analysis. For polyhydrogensiloxanes and reaction products thereof it is preferred to determine the total weight of the at least one hydrophobising agent on the total surface of the at least one alkine earth metal carbonate-comprising materiel by inductively coupled plasma mass spectroscopy (ICP-MS), as described in the experimental section.

According to one embodiment, the specific surface area (BET) of the least one alkaline earth metal carbonate-comprising material is from 1 to 150 m$^2$/g, preferably from 2 to 60 m$^2$/g, and more preferably from 2 to 15 m$^2$/g, as measured using nitrogen and the BET method according to ISO 9277, and/or the total weight of copper on the total surface area of the at least one alkaline earth metal carbonate-comprising material is from 0.001 to 300 mg/m$^2$, preferably from 0.1 to 100 mg/m$^2$, and more preferably from 1.5 to 30 mg/m$^2$; and/or the total weight of the at least one hydrophobising agent on the total surface area of the alkaline earth metal carbonate-comprising material is from 0.001 to 9 mg/m$^2$, preferably from 0.01 to 8 mg/m$^2$, and more preferably from 0.1 to 4 mg/m$^2$. According to one embodiment the at least one hydrophobising agent is selected from the group consisting of an aliphatic carboxylic acid having a total amount of carbon atoms from $C_4$ to $C_{24}$ and/or reaction products thereof, a mono-substituted succinic anhydride consisting of succinic anhydride mono-substituted with a group selected from a linear, branched, aliphatic and cyclic group having a total amount of carbon atoms from at least $C_2$ to $C_{30}$ in the substituent and/or reaction products thereof, a phosphoric acid ester blend of one or more phosphoric acid mono-ester and/or reaction products thereof and one or more phosphoric acid di-ester and/or reaction products thereof, polyhydrogensiloxane and reaction products thereof, an inert silicone oil, preferably polydimethylsiloxane, and mixtures thereof.

The modified mineral-based filler may be used for various applications.

According to one embodiment, the modified mineral-based filler according to the present invention is used in polymer applications, paper coating applications, paper making, paints, coatings sealants, printing inks, adhesives, food, feed, pharmaceuticals, concrete, cement, cosmetics, engineered wood applications, plasterboard applications, water treatment, packaging applications and/or agricultural applications, wherein preferably the modified-based filler is a dried modified mineral-based filler. Engineered wood applications may comprise the use in engineered wood products such as wood composites materials, preferably medium density fibreboards or chipboards.

According to another embodiment, the modified mineral-based filler according to the present invention is used as preservative, wherein preferably the modified-based filler is a dried modified mineral-based filler.

A preservative is a compound which can protect a substrate, dry and/or wet, from spoilage and/or degradation and/or destruction, and/or defacement and/or visible disfigurement due to the action of microorganisms and/or prevent growth of microorganisms on a substrate and/or in a substrate and/or prevent contamination of a substrate by microorganisms and/or prevent settlement of microorganisms on a substrate. According to a preferred embodiment, the preservative acts as a dry-film-preservative. The substrate is preferably in a solid state, such as a paper surface, a wood surface, a wall, the surface of a packaging material or the surface of a polymer article, but can also be in a wet state such as in an aqueous suspension.

The modified mineral-based filler according to the present invention can also be used for enhancing and/or mediating the antimicrobial activity of a substrate, e.g. a sheet of paper, a cardboard, a polymer material, a paint, a wood surface, concrete, or a plant. According to a preferred embodiment, the antimicrobial activity is against at least one strain of bacteria and/or at least one strain of mould and/or at least one strain of yeast and/or at least one algae. Antimicrobial activity of a compound refers to a reduction of growth of microorganism and/or a reduction of viable microorganisms apparent in the presence of said compound. The expression "enhancing the antimicrobial activity" means that the antimicrobial activity of the substrate containing the inventive modified mineral-based filler is higher than the antimicrobial activity compared to a substrate not containing said filler. The expression "for mediating the antimicrobial activity of a substrate" means that no antimicrobial activity is apparent in a substrate without the inventive modified mineral-based filler.

According to one embodiment, the substrate is a paper, a cardboard, a polymer material, a paint, a wood surface, concrete, or a plant. According to one embodiment, the polymer material is a polymer film. A "film" in the meaning of the present invention is a sheet or layer of material having a median thickness which is small compared to its length and width. For example, the term "film" may refer to a sheet or layer of material having a median thickness of less than 200 μm, but more than 1 μm.

According to one embodiment the at least one strain of bacteria is selected from the group consisting of *Escherichia* sp., *Staphylococcus* sp., *Thermus* sp., *Propionibacterium* sp., *Rhodococcus* sp., *Panninobacter* sp., *Caulobacter* sp., *Brevundimonas* sp., *Asticcacaulis* sp., *Sphingomonas* sp., *Rhizobium* sp., *Ensifer* sp., *Bradyrhizobium* sp., *Tepidimonas* sp., *Tepidicella* sp., *Aquabacterium* sp., *Pelomonas* sp., *Alcaligenis* sp., *Achromobacter* sp., *Ralstonia* sp., *Limnobacter* sp., *Massilia* sp., *Hydrogenophaga* sp., *Acidovorax* sp., *Curvibacter* sp., *Delftia* sp., *Rhodoferax* sp., *Alishewanella* sp., *Stenotrophomonas* sp., *Dokdonella* sp., *Methylosinus* sp., *Hyphomicrobium* sp., *Methylosulfomonas* sp., *Methylobacteria* sp., *Pseudomonas* sp. such as *Pseudomonas mendocina*, *Enterococcus* sp., *Myroides* sp., *Burkholderia* sp., *Alcaligenes* sp. *Staphylococcus* sp. such as *Staphylococcus aureus*, *Escherichia* sp. such as *Escherichia coli*, and mixtures thereof.

According to one embodiment the at least one strain of mould is selected from the group comprising of *Acremonium* sp., *Alternaria* sp., *Aspergillus* sp. such as *Aspergillus niger*, *Aureobasidium* sp., such as *Aureobasidium pullulans*, *Cladosporium* sp., *Fusarium* sp., *Mucor* sp., *Penicillium* sp., such as *Penicillium funiculosum*, *Rhizopus* sp., *Stachybotrys* sp., *Trichoderma* sp., *Dematiaceae* sp., *Phoma* sp., *Eurotium* sp., *Scopulariopsis* sp., *Aureobasidium* sp., *Monilia* sp., *Botrytis* sp., *Stemphylium* sp., *Chaetomium* sp., *Mycelia* sp., *Neurospora* sp., *Ulocladium* sp., *Paecilomyces* sp., *Wallemia* sp., *Curvularia* sp., and mixtures thereof.

According to one embodiment the at least one strain of yeast is selected from the group comprising Saccharomycotina, Taphrinomycotina, Schizosaccharomycetes, Basidiomycota, Agaricomycotina, Tremellomycetes, Pucciniomycotina, Microbotryomycetes, *Candida* sp. such as *Candida albicans*, *Candida tropicalis*, *Candida stellatoidea*, *Candida glabrata*, *Candida krusei*, *Candida guilliermondii*, *Candida viswanathii*, *Candida lusitaniae* and mixtures thereof, *Yarrowia* sp. such as *Yarrowia lipolytica*, *Cryptococcus* sp. such as *Cryptococcus gattii* and *Cryptococcus neofarmans*, *Zygosaccharomyces* sp., *Rhodotorula* sp. such as *Rhodotorula mucilaginosa*, and mixtures thereof.

According to a preferred embodiment of the present invention, the at least one strain of bacteria is selected from the group consisting of *Escherichia coli*, *Staphylococcus aureus*, *Pseudomonas putida*, *Pseudomonas mendocina*, *Pseudomonas oleovorans*, *Pseudomonas fluorescens*, *Pseudomonas alcaligenes*, *Pseudomonas pseudoalcaligenes*, *Pseudomonas entomophila*, *Pseudomonas syringae*, *Methylobacterium extorquens*, *Methylobacterium radiotolerants*, *Methylobacterium dichloromethanicum*, *Methylobacterium organophilu*, *Hyphomicrobium zavarzini*, *Enterococcus faecalis*, *Myroides odoratus*, *Pseudomonas aeruginosa*, *Pseudomonas orizyhabitans*, *Burkholderia cepacia*, *Alcaligenes faecalis* and *Sphingomonas paucimobilis* and mixtures thereof and/or the at least one strain of mould is selected from the group comprising of *Penicillium funiculosum*, *Aspergillus niger*, *Aureobasidium pullulans*, *Alternaria alternate*, *Cladosporium cladosporioides*, *Phoma violaceae*, *Ulocladium atrum*, *Aspergillus versicolor*, *Stachybotris chartarum*, *Penicillium purpurogenum*, *Rhodotorula mucilaginosa* and/or the at least one strain of yeast is selected from the group of *Candida albicans* and/or the at least one strain of alga is selected from the group of *Nostoc commune*, *Gloeocapsa alpicola* (syn. *Anacystis* montana), *Klebsormidium flaccidum*, *Stichococcus bacillaris*, *Pseudokirchneriella subcapitata*, *Desmodesmus subspicatus*, *Navicula pelliculosa*, *Anabaena flosaquae*, *Synechococcus leopoliensis*, and mixtures thereof.

According to still another embodiment, the modified mineral-based filler according to the present invention is used for enhancing the electrical conductivity of a substrate, wherein preferably the modified-based filler is a dried modified mineral-based filler.

The inventive modified mineral-based filler may be incorporated into an article in order to provide an article with enhanced antimicrobial activity and/or enhanced electrical conductivity. According to a further aspect of the present invention, an article is provided comprising a modified mineral-based filler according to the present invention, wherein the article is selected from paper products, engineered wood products, plasterboard products, polymer products, hygiene products, medical products, healthcare products, filter products, woven materials, nonwoven materials, geotextile products, agriculture products, horticulture products, clothing, footwear products, baggage products, household products, industrial products, packaging products, building products, and construction products.

The scope and interest of the invention will be better understood based on the following examples which are intended to illustrate certain embodiments of the present invention and are non-limitative.

EXAMPLES

1. Measurement Methods

In the following, measurement methods implemented in the examples are described.

Solid Content

The suspension solids content (also known as "dry weight") was determined using a Moisture Analyser MJ33 (Mettler-Toledo, Switzerland), with the following settings: drying temperature of 150° C., automatic switch off if the mass does not change more than 1 mg over a period of 30 sec, standard drying of 5 to 20 g of suspension.

Water Pick-Up

The moisture pick up susceptibility of a material as referred to herein is determined in mg moisture/g after exposure to an atmosphere of 10 and 85% relative humidity, respectively, for 2.5 hours at a temperature of +23° C. (±2° C.). For this purpose, the sample is first kept at an atmosphere of 10% relative humidity for 2.5 hours, then the atmosphere is changed to 85% relative humidity at which the sample is kept for another 2.5 hours. The weight increase between 10 and 85% relative humidity is then used to calculate the moisture pick-up in mg moisture/g of sample.

Moisture Content

The moisture content has been determined on a Karl-Fischer Coulometer (C 30 oven:

Mettler Toledo Stromboli, Mettler Toledo, Switzerland) at 220° C. under nitrogen (flow 80 mL/min, heating time 10 min). The accuracy of the result was checked with a HYDRANAL-Water Standard KF-Oven (Sigma-Adrich, Germany), measured at 220° C.).

X-Ray Fluorescence Analysis (XRF)

11.5 g dry sample were pressed to a tablet, using a press at 400 kN. The elemental composition of the sample was measured by sequential, wavelength dispersive X-ray fluorescence (using an ARL™ PERFORM'X X-ray fluorescence spectrometer, Thermo Fisher Scientific, Inc., USA). The quantification was made by means of a calibration which was especially prepared for calcium carbonate.

Ion Chromatography

Anions were determined by ion chromatography (882 Compact IC plus, Metrohm).

Inductively Coupled Plasma Mass Spectrometry (ICP-MS) Analysis

The modified mineral based filler was dissolved in a microwave assisted nitric acid based digestion process. The solution was analyzed by ICP-MS (Measured with an ELAN DRC-e from Perking Elmer). Commercially available multi-element calibration solutions were used for quantification of the formed water insoluble copper salts and copper minerals.

X-Ray Diffraction (XRD)

XRD experiments were performed on the samples using rotatable PMMA holder rings. Samples were analyzed with a Bruker D8 Advance powder diffractometer obeying Bragg's law. This diffractometer consists of a 2.2 kW X-ray tube, a sample holder, a ϑ-ϑ-goniometer, and a VANTEC-1 detector. Nickel-filtered Cu Kα radiation was employed in all experiments. The profiles were chart recorded automatically using a scan speed of 0.7° per minute in 24. The resulting powder diffraction pattern can easily be classified by mineral content using the DIFFRACsuite software packages EVA and SEARCH, based on reference patterns of the ICDD PDF 2 database. Quantitative analysis of diffraction data refers to the determination of amounts of different phases in a multi-phase sample and has been performed using the DIFFRACsuite software package TOPAS. In detail, quantitative analysis allows to determine structural characteristics and phase proportions with quantifiable numerical precision from the experimental data itself. This involves modelling the full diffraction pattern (Rietveld approach, e.g. described in Bish, D. L. & Howard, S. A., Quantitative Phase Analysis Using the Rietveld Method, J. Appl. Cryst. 21, 1988, 86-91) such that the calculated pattern(s) duplicates the experimental one. The Rietveld method requires knowledge of the approximate crystal structure of all phases of interest in the pattern. However, the use of the whole pattern rather than a few select lines produces accuracy and precision much better than any single-peak-intensity based method.

Brookfield Viscosity

The Brookfield viscosity was measured by a Brookfield (Type RVT) viscometer at 24° C.±3° C. at 100 rpm using an appropriate spindle of the Brookfield RV-spindle set and is specified in mPa·s. Once the spindle has been inserted into the sample, the measurement is started with a constant rotating speed of 100 rpm. The reported Brookfield viscosity values are the values displayed 60 seconds after the start of the measurement. Based on his technical knowledge, the skilled person will select a spindle from the Brookfield RV-spindle set which is suitable for the viscosity range to be measured. For example, for a viscosity range between 200 and 800 mPa·s the spindle number 3 may be used, for a viscosity range between 400 and 1 600 mPa·s the spindle number 4 may be used, and for a viscosity range between 800 and 3 200 mPa·s the spindle number 5 may be used.

pH pH was measured on a Mettler-Toledo Seven-Multi device. The pH of a suspension was measured at 24° C.±3° C. using a Mettler Toledo Seven Easy pH meter and a Mettler Toledo InLab® Expert Pro pH electrode (Mettler Toledo, Switzerland). A three point calibration (according to the segment method) of the instrument was first made using commercially available buffer solutions having pH values of 4, 7 and 10 at 20° C. (from Aldrich). The reported pH values are the endpoint values detected by the instrument (the endpoint is when the measured signal differs by less than 0.1 mV from the average over the last 6 seconds).

Conductivity

The conductivity of a suspension was measured at 24° C.±3° C. using Mettler Toledo Seven Multi instrumentation equipped with the corresponding Mettler Toledo conductivity expansion unit and a Mettler Toledo InLab® 730 conductivity probe (Mettler Toledo, Switzerland).

The instrument was first calibrated in the relevant conductivity range using commercially available conductivity calibration solutions from Mettler Toledo. The influence of temperature on conductivity is automatically corrected by the linear correction mode. The measured conductivities are reported for the reference temperature of 20° C. The reported conductivity values are the endpoint values detected by the instrument (the endpoint is when the measured conductivity differs by less than 0.4% from the average over the last 6 seconds).

Antimicrobial Surface Activity Test

Fresh bacteria cultures of the bacteria *Escherichia coli* DSM 1576 and *Staphylococcus aureus* strains DSM 346 were prepared by dilution streaking onto a tryptic soy agar plate (TSA, no. 236950, Becton Dickinson and Company, USA) and incubation for 16 to 20 h at 35° C.

To test the antimicrobial surface activity, the Japanese Standard Protocol JIS Z 2801 2000 was followed using fresh bacteria prepared as described above. The plating, counting and evaluation were done according to the Japanese Standard Protocol JIS Z 2801 2000 with the following amendments. To confirm results, studies were performed with a single test piece instead of triplicates. For all coated samples, the bacteria were released after incubation from the test item in a petri dish using a sterile Drigalski spatula to massage the test item with medium, instead of using a stomacher bag and massaging the item by hand. Further for coated samples the test items were not sterilized with 70% ethanol prior analysis.

As described in the Japanese Standard Protocol JIS Z 2801 2000, the bacterial counts are reported as colony forming units per test item (cfu/test item) with 10 cfu/test item as limit of detection (LOD). Thereof the antimicrobial activity (R) of the test items was calculated as described in the Japanese Standard Protocol JIS Z 2801 2000. For it, after 24 h incubation at 35° C., the average number of viable bacteria on the test item (B) and the untreated control (A) are used to calculate the antimicrobial activity (R) using the following formula: R=$\log_{10}$(A/B). If zero cfu were detected, a value of 10 cfu/test item was used for calculation of the limit of detection of the antimicrobial activity.

Fungal Growth Resistance Test

Fresh cultures of fungi (e.g. *Aspergillus niger* ATCC 6275, *Aureobasidium pullulans* ATCC 9348, *Penicillium funiculosum* ATCC 11797) were prepared by inoculation of malt agar plates (malt extract broth, no. 1.05397, Merck KGaA, Germany) containing 1.5 wt.-% agar (no. 05039, Fluka, Switzerland) with spores and/or mycelia of fungi and incubation at 25° C. for until malt agar plate is fully covered with spores (approximately 1 week). Such culture techniques are well known to the skilled person and are described for instance in ASTM D5590-00.

Malt extract broth (no. 1.05397, Merck KGaA, Germany) was inoculated with loop of spores from a fresh fungal malt agar plate. Spores were dispersed by mixing until no clumps were visible. Test items were cut to 2.5 cm×9 cm and immersed into the spore-dispersion, drained and placed into 50 ml bioreactor tubes with a gas permeable filter (e.g. TPP TubeSpin® Bioreactors, TPP, Switzerland). Test items in the bioreactors were incubated upright at 28° C. and 90% relative humidity. After different incubation times the percentage of fungal defacement was rated analogous to the rating system of ASTM D3273-D12.

A rating of 10=0 defacement (no growth detectable).
A rating of 9=1 to 10% defacement.
A rating of 8=11 to 20% defacement.
A rating of 7=21 to 30% defacement.
A rating of 6=31 to 40% defacement.
A rating of 5=41 to 50% defacement.
A rating of 4=51 to 60% defacement.
A rating of 3=61 to 70% defacement.
A rating of 2=71 to 80% defacement.
A rating of 1=81 to 90% defacement.
A rating of 0=91 to 100% defacement.

The Antialgal Efficacy Test

The antialgal efficacy was determined according to the test norm DIN EN 15458:2007 (Paint and varnishes—Laboratory test method for testing the efficacy of film preservatives in a coating against algae) using *Stichococcus bacillaris* as test organism. The principle of the semi-quantitative test method is that the coating sample containing the film preservative, or the untreated control, is placed onto a nutrient agar surface with the coating faced-up. Then the surface is inoculated with a standard algal spore suspension and incubated. At four different time points (after 14, 21, 28 and 35 days) the intensity of the algal growth on the surface of the coating sample and the algal growth on the agar (surrounding the test pieces) is evaluated and compared to the control using the following rating system.

0: No algal growth on the surface of the coating sample
1: less algal growth on the coating sample containing modified mineral-based filler compared to sample containing untreated mineral.
2. equal or more algal growth on the coating sample containing modified mineral-based filler compared to sample containing untreated mineral.

The test norm was performed in triplicates with a few minor amendments: 1) All coating samples were not conditioned according to EN23270 for 5 days at 23+/−2° C. and 50+/−5% relative humidity but instead stored for several weeks at 23+/−2° C. without controlled humidity. 2) All coating samples were not sterilized prior testing. 3) The size and shape of all coating samples was rectangular (25 mm×50 mm) instead of circular (55 mm diameter). The final evaluation was carried out at day 32.

Pigment Whiteness R457

Pigment whiteness R457 was measured on a tablet (prepared on a press with a pressure of 4 bar for 15 seconds) using an ELREPHO 3000 spectrophotometer (Datacolor AG, Switzerland) according to ISO 2469:1994 (DIN 53145-2:2000 and DIN 53146:2000).

CIELAB Coordinates

The CIELAB L*, a*, b* coordinates were measured using an ELREPHO 3000 spectrophotometer (Datacolor AG, Switzerland) according to EN ISO 11664-4 and barium sulphate as standard.

Yellow Index

The CIE coordinates were measured using an ELREPHO 3000 spectrophotometer (Datacolor AG, Switzerland). The yellow index (=YI) was calculated by the following formula:

$$YI=100*(R_x-R_z)/R_y).$$

2. Preparation of Copper Salt Solutions and Copper Salt Suspensions

Solution 1

80 g of deionized water was provided in a beaker glass, and 25 g copper sulphate (anhydrous, Sigma-Aldrich, Spain) was added slowly, under strong stirring. The resulting deep blue mixture was stirred 2 h at room temperature and then filtered. The solid content of the obtained solution was between 20 and 24 wt.-%, based on the total weight of the solution.

Solution 2

80 g of deionized water was provided in a beaker glass, and 39 g copper sulphate (pentahydrate, Sigma-Aldrich, Spain) was added slowly, under strong stirring. The resulting deep blue mixture was stirred 2 h at room temperature and then filtered. The solid content of the obtained solution was between 20 and 24 wt.-%, based on the total weight of the solution.

Solution 3:

480 g of copper (II) nitrate (trihydrate, Sigma-Aldrich, Spain) was provided in a beaker glass, and 200 g deionised water was added slowly. The resulting deep blue mixture was stirred 2 h at room temperature and then filtered. The solid content of the obtained solution was 41.1 wt.-%, based on the total weight of the solution.

Suspension 1

60 g of deionized water was provided in a beaker glass, and 42 g copper sulphate (anhydrous, Sigma-Aldrich, Spain) was added slowly, under strong stirring. The resulting deep blue mixture was stirred 2 h at room temperature and was not fully dissolved. The solid content of the obtained suspension was 42 wt.-%, based on the total weight of the suspension.

3. Preparation of Modified Mineral-Based Filler

In the following description of the preparation of the Examples and Comparatives Examples the indication of weight in form of "parts" always refers to "parts by weight", unless indicated otherwise.

3.1. Example 1—Powder 1

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 1 part relative to 100 parts CaCO$_3$ of copper sulphate (45.2 g of solution 1 having 22.1 wt.-% solid content) was introduced and stirring was continued for another 20 minutes (120° C., 3 000 rpm). After that time, the mixture was allowed to cool and collected. A slightly green homogeneous powder was obtained (Powder 1).

3.2. Example 2—Powder 2

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 0.4 parts relative to 100 parts CaCO$_3$ of copper sulphate (17.5 g of solution 1 having 22.9 wt.-% solid content) was introduced and stirring was continued for another 20 minutes (120° C., 3 000 rpm). After that time, the mixture was allowed to cool and collected. A slightly green homogeneous powder was obtained (Powder 2).

3.3. Example 3—Powder 3

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 0.1 parts of copper sulphate (4.5 g of solution 1 having 22.1 wt.-% solid content) relative to 100 parts CaCO$_3$ was introduced and stirring was continued for another 20 minutes (120° C., 3 000 rpm). After that time, the mixture was allowed to cool and collected. A very slightly green homogeneous powder was obtained (Powder 3).

3.4. Example 4—Powder 4

0.75 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 3 parts of copper sulphate (4.5 g of suspension 1 having 42 wt.-% solid content) relative to 100 parts CaCO$_3$ was introduced and stirring was continued for another 20 minutes (120° C., 3 000 rpm). After that time, the mixture was allowed to cool and collected. A strongly green powder was obtained (Powder 4).

3.5. Example 5—Powder 5

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 0.4 parts of copper sulphate (18.2 g of solution 2 having 22 wt.-% solid content) relative to 100 parts CaCO$_3$ was introduced and the mixing was continued for another 20 minutes (120° C., 3 000 rpm). After that time, the mixture was allowed to cool and collected. A slightly green homogeneous powder was obtained. The powder was then washed with 1 L deionized water, and filtered. A sample of the filtrate and the filter cake was then collected and analysed (XRF). This washing procedure has been repeated 3 times. At the end, the filtered powder was dried in the oven under reduced pressure (Powder 5).

3.6. Example 6—Powder 6

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 10 minutes (3 000 rpm, 120° C.). After that time, 1 part of copper sulphate (50 g of solution 2 having 20 wt.-% solid content) relative to 100 parts CaCO$_3$ was introduced and stirring was continued for another 20 minutes (120° C., 3 000 rpm). Then, 0.6 parts of stearic acid (Omyacid 54, Omya AG, Switzerland) relative to 100 parts CaCO$_3$ was introduced and stirring was continued for another 20 minutes (120° C., 3 000 rpm). After that time, the mixture was allowed to cool and collected. A slightly green powder was obtained (Powder 6).

3.7. Example 7—Powder 7

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH), and conditioned by stirring for 10 minutes (3 000 rpm, 120° C., Germany). After that time, 0.6 parts of stearic acid (Omyacid 54, Omya AG, Switzerland) and 1 part of copper sulphate (50 g of solution 2 having 20 wt.-% solid content) relative to 100 parts CaCO$_3$ were introduced and the mixing was continued for another 20 minutes (120° C., 3 000 rpm). After that time, the mixture was allowed to cool and collected. A slightly green powder was obtained (Powder 7).

3.8. Example 8—Powder 8

A suspension of 150 g of dry ground calcium carbonate from Italy ($d_{50}$=2.6 µm, BET specific surface area=2.6 m$^2$/g) in deionized water (450 mL) was placed in a round bottom flask equipped with a condenser and an addition funnel. The mixture was heated to 90° C. and a previously prepared solution of 35 g of copper sulphate pentahydrate in water (150 ml) was added dropwise to the mixture. The suspension turned green in colour, and heating was continued for another 2 h (with stirring at 500 rpm) after completion of the addition. The heating was then stopped and the suspension was filtered on a Buchner funnel, and washed with 1 L deionized water. The filtrate was colourless, and the filter cake (green powder) was then dried in an oven (80° C., reduced pressure). The obtained green powder (Powder 8) was then analyzed by XRD.

3.9. Example 9—Powder 9

1.00 kg of a wet ground and spray dried marble from Carrara, Italy ($d_{50}$=1.6 µm, BET specific surface area=4.1 m$^2$/g) was placed in a high speed mixer (MTI Mixer, MTI Mischtechnik International GmbH, Germany), and conditioned by stirring for 10 minutes (3 000 rpm, 120° C.). After that time, 0.4 parts relative to 100 parts $CaCO_3$ of copper sulphate (20 g of solution 2 having 20 wt.-% solid content) was introduced and stirring was continued for another 20 minutes (120° C., 3 000 rpm). After that time, the mixture was allowed to cool and collected. A slightly green homogeneous powder was obtained (Powder 9).

3.10. Example 10—Powder 10

1.00 kg of a wet ground and spray dried marble from Carrara, Italy ($d_{50}$=1.6 µm, BET specific surface area=4.1 m$^2$/g) was placed in a high speed mixer (MTI Mixer, MTI Mischtechnik International GmbH, Germany), and conditioned by stirring for 10 minutes (3 000 rpm, 120° C.). After that time, 0.05 parts relative to 100 parts $CaCO_3$ of copper sulphate (2.5 g of solution 2 having 20 wt.-% solid content) was introduced and stirring was continued for another 20 minutes (120° C., 3 000 rpm). After that time, the mixture was allowed to cool and collected. A very slightly green homogeneous powder was obtained (Powder 10).

3.11. Example 11—Powder 11

400 g of a wet ground and spray dried marble from Carrara, Italy ($d_{50}$=1.6 µm, BET specific surface area=4.1 m$^2$/g) was placed in a mixer (Somakon MP-LB Mixer, Somakon Verfahrenstechnik, Germany), and conditioned by stirring for 10 minutes (2 000 rpm, 120° C.). After that time, 0.02 parts relative to 100 parts $CaCO_3$ of copper sulphate (8 g of solution 2 previously diluted to 1 wt.-% solids content) was added dropwise over 2 minutes. Stirring and heating was continued for another 20 minutes after completion of the addition (120° C., 2 000 rpm). After that time, the mixture was allowed to cool and the powder collected (Powder 11).

3.12. Example 12—Powder 12

1 kg of a wet ground and spray dried marble from Carrara, Italy ($d_{50}$=1.6 µm, BET specific surface area=4.1 m$^2$/g) was placed in a 5 L beaker equipped with a mechanical overhead stirrer. 3 L of deionised water was added, and the mixture was heated to 80° C. for 1 h (stirring at approximately 300 rpm). After that time, 243.3 g of the copper nitrate solution 3 (equivalent to 10 parts solid relative to 100 parts $CaCO_3$) was added dropwise to the mixture via an addition funnel. The resulting suspension was then heated for 2 h at 80° C./300 rpm, and the suspension was then filtered on a Buchner funnel. The filter cake was redispersed (with 3 L deionised water), stirred, and filtered again to wash off soluble salts. The washing procedure was repeated a second time and the filter cake was then dried in an oven (120° C., 7 h) to obtain a green powder after deagglomeration (Powder 12).

3.13. Example 13—Powder 13

1 kg of a dry ground calcium carbonate from Italy ($d_{50}$=1.7 µm, BET specific surface area=3.8 m$^2$/g) was placed in a 5 L beaker equipped with a mechanical overhead stirrer. 3 L of deionised water was added, and the mixture was heated to 70-80° C. (stirring at approximately 300 rpm). Once this temperature was reached, 500 g of a 20 wt.-% copper sulphate solution 2 (equivalent to 10 parts solid relative to 100 parts $CaCO_3$) was added dropwise to the mixture via an addition funnel. The resulting green suspension was then heated for 3 h at 80° C./300 rpm, and the suspension was then cooled down, and filtered on a Buchner funnel. The filter cake was redispersed (with 2 L deionised water), stirred for 1 h (300 rpm), and filtered again to wash off soluble salts. The washing procedure was repeated a second time and the filter cake was then dried in an oven (110° C., 7 h) to obtain a green powder after deagglomeration (Powder 13).

3.14. Example 14—Powder 14

In a 1 L flask equipped with a condenser and an addition funnel was introduced 220 g of a dry ground calcium carbonate from Italy ($d_{50}$=2.6 µm, BET specific surface area=2.6 m$^2$/g) and 440 g of deionized water. The mixture was stirred (600 rpm) and heated to 100° C. 110 g of a 20 wt.-% solid content copper sulphate solution 2 (equivalent to 10 parts solid relative to 100 parts $CaCO_3$) was then added dropwise at 100° C. After addition, the green suspension is heated for 3 h at 100° C. under vigorous stirring. The mixture is then cooled and filtered on a Buchner funnel, washed 3 times with 1 L deionised water and dried in oven (90° C., reduced pressure), (Powder 14).

3.15. Example 15—Powder 15

In a 1 L flask equipped with a condenser and an addition funnel was introduced 220 g of a dry ground calcium carbonate from Austria ($d_{50}$=7.5 µm, BET specific surface area=2.2 m$^2$/g) and 440 g of deionized water. The mixture was stirred (600 rpm) and heated to 100° C. 110 g of a 20 wt.-% solid content copper sulphate solution 2 (equivalent to 10 parts solid relative to 100 parts $CaCO_3$) was then added dropwise at 100° C. After addition, the green suspension is heated for 3 h at 100° C. under vigorous stirring. The mixture is then cooled and filtered on a Buchner funnel, washed 3 times with 1 L deionised water and dried in oven (90° C., reduced pressure), (Powder 15).

3.16. Example 16—Powder 16

1.00 kg of dry ground calcium carbonate from Italy ($d_{50}$=2.6 µm, BET specific surface area=2.6 m$^2$/g) was placed in a high speed mixer (MTI Mixer, MTI Mischtechnik International GmbH, Germany), and conditioned by stirring for 20 minutes (3 000 rpm, 120° C.). After that time, 1.0 parts of copper sulphate (50 g of solution 2 having 20 wt.-% solids content) relative to 100 parts $CaCO_3$ was introduced and the mixing was continued for another 20 minutes (120° C., 3 000 rpm). After that time, the mixture was allowed to cool and collected. A slightly green homogeneous powder was obtained (Powder 16).

3.17. Example 17—Powder 17

0.9 kg of powder 16 was dispersed in 1.5 L deionized water, stirred at room temperature for 1 hour, and filtered on a Buchner funnel. This washing procedure was repeated 4 times. At the end, the filtered powder was dried in the oven (90° C.) under reduced pressure (Powder 17).

3.18. Example 18—Powder 18

1.00 kg of dry ground calcium carbonate from Austria ($d_{50}$=7.5 µm, BET specific surface area=2.2 m²/g) was placed in a high speed mixer (MTI Mixer, MTI Mischtechnik International GmbH, Germany), and conditioned by stirring for 20 minutes (3 000 rpm, 120° C.). After that time, 1.0 parts of copper sulphate (50 g of solution 2 having 20 wt.-% solid content) relative to 100 parts $CaCO_3$ was introduced and the mixing was continued for another 20 minutes (120° C., 3 000 rpm). After that time, the mixture was allowed to cool and collected. A slightly green homogeneous powder was obtained. (Powder 18).

3.19. Example 19—Powder 19

0.9 kg of powder 18 was dispersed in 1.5 L deionized water, stirred at room temperature for 1 hour, and filtered on a Buchner funnel. This washing procedure was repeated 4 times. At the end, the filtered powder was dried in the oven (90° C.) under reduced pressure (Powder 19)

3.20. Comparative Example 1—Powder C1

Comparative Example 1 is a ground calcium carbonate from Italy ($d_{50}$=2.6 µm, BET specific surface area=2.6 m²/g), without further treatment (Powder C1).

3.21. Comparative Example 2—Powder C2

1.00 kg of dry ground calcium carbonate from Italy ($d_{50}$=2.6 µm, BET specific surface area=2.6 m²/g) was placed in a closed high speed mixer (MTI Mixer, MTI Mischtechnik International GmbH, Germany), and conditioned by stirring for 10 minutes (3 000 rpm, 120° C.). After that time, 0.6 parts of stearic acid (Omyacid 54, Omya AG, Switzerland) relative to 100 parts $CaCO_3$ were introduced and mixing was continued for another 20 minutes (120° C., 3 000 rpm). After that time, the mixture was allowed to cool and collected. A slightly green powder was obtained (Powder C2).

3.22. Comparative Example 3—Powder C3

Comparative Example 3 is a wet ground and spray dried calcium carbonate from Carara Italy ($d_{50}$=1.6 µm, BET specific surface=4.1 m²/g), without further treatment (Powder C3).

3.23. Comparative Example 4—Powder C4

Powder C4 is a dry ground calcium carbonate from Italy ($d_{50}$=1.7 µm, BET specific surface area=3.8 m²/g).

The prepared modified mineral-based fillers are summarized in Table 1 below. Furthermore, the physical and chemical properties of selected modified mineral-based fillers were tested. The results are shown in Tables 2 to 5 below.

TABLE 1

Overview of prepared modified mineral-based fillers.

| Powder | $CuSO_4/CuNO_3$[a] [wt.-%, based on total weight of $CaCO_3$] | Stearic acid [parts per hundred parts $CaCO_3$] | comments | Moisture Content |
|---|---|---|---|---|
| C1 | — | — | — | 1 497 ppm |
| C2 | — | 0.6 | — | — |
| C3 | — | — | — | — |
| C4 | — | — | — | — |
| 1 | 1 | — | — | 2 418 ppm |
| 2 | 0.4 | — | — | — |
| 3 | 0.1 | — | — | 1 497 ppm |
| 4 | 3 | — | — | 4 469 ppm |
| 5 | 0.4 | — | Powder washed with water | — |
| 6 | 1 | 0.6 | Successive addition | — |
| 7 | 1 | 0.6 | Simultaneous addition | — |
| 8 | 15 | — | Wet process | 2.37 wt.-% |
| 9 | 0.4 | — | — | — |
| 10 | 0.05 | — | — | — |
| 11 | 0.02 | — | — | — |
| 12[a] | 10 | — | Wet process | — |
| 13 | 10 | — | Wet process | — |
| 14 | 10 | — | Wet process | — |
| 15 | 10 | — | Wet process | — |
| 16 | 1 | — | — | — |
| 17 | 1 | — | Washed powder | — |
| 18 | 1 | — | — | — |
| 19 | 1 | — | Washed powder | — |

[a]Sample 12 marked with a) has been prepared by using $CuNO_3$ the remaining ones are prepared by using $CuSO_4$ as starting material.

TABLE 2

Water pick-up and brightness data.

| Powder | Water pick-up (mg/g) | Brightness | | | R457 TAPPI | Yellowness index | CIELAB | | |
|---|---|---|---|---|---|---|---|---|---|
| | | Rx | Ry | Rz | | | L* | a* | b* |
| C1 | 1.7 | 95.1 | 94.8 | 93.5 | 93.6 | 1.7 | 97.9 | 0.05 | 0.90 |
| 2 | 1.9 | 92.6 | 93.3 | 92.5 | 92.7 | 0.3 | 97.4 | −1.11 | 0.61 |
| 3 | 1.6 | 94.4 | 94.3 | 93.2 | 93.3 | 1.3 | 97.8 | −0.27 | 0.81 |
| 13 | 3.4 | — | — | — | — | — | — | — | — | n.d. = not determined.

TABLE 3

XRF analysis of composition of powder 5 after washing with 1-4 L of deionized water (room temperature, 60 minutes) and powder C1.

|  | Powder C1 [wt.-%] | Powder 5 before washing [wt.-%] | Powder 5 after 1 L $H_2O$ washing [wt.-%] | Powder 5 after 2 L $H_2O$ washing [wt.-%] | Powder 5 after 4 L $H_2O$ washing [wt.-%] |
|---|---|---|---|---|---|
| $CaCO_3$ | 97.7 | 97.6 | 97.7 | 97.7 | 97.8 |
| other constituents | 2.3 | 2.4 | 2.3 | 2.3 | 2.2 |
| Cu (semiquant by UNIQUANT) | *<0.001 | 0.15 | 0.15 | 0.15 | 0.15 |

*approx. 0.001% (10 ppm) is the detection limit of the semiquant. XRF analysis.

TABLE 4a

Composition of filtered washing water from powder 5.

|  | After 1 L washing | After 2 L washing | After 4 L washing |
|---|---|---|---|
| Sulphate (Ion Chromatogr.) | 688 ppm ROR[a]: 99.1% | 195 ppm | 29 ppm |
| Cu (ICP-MS) | 0.2 ppm | <0.1 ppm | <0.1 ppm |

[a]ROR means rate of recovery of the measurement.

4 samples of 15 g of Powder 8 were suspended in 150 g deionized water in a glass bottle. After 1 h, 24 h, 4 days and 4 weeks, the supernatant was filtered and analysed by ICP-MS and Ion chromatography to determine the amount of copper solubilized.

TABLE 4b

Composition of filtered washing water from powder 8.

|  | After 1 h | After 24 h | After 4 days | After 1 month |
|---|---|---|---|---|
| Sulphate (Ion Chromatogr.) | 1436 ppm | 1431 ppm | 1467 ppm (ROR: 101.2%)a | 1485 ppm |
| Cu (ICP-MS) | 24 ppb | 14 ppb | 20 ppb | 22 ppb | aROR means rate of recovery of the measurement.

As can be gathered from Tables 3 and 4 a significant amount of copper has been incorporated into the calcium carbonate surface. Furthermore, only a minor amount of the copper has been leached after washing.

TABLE 5a

Quantitative Rietveld analyses (XRD) of the powders 1, 4, and 8.

| Mineral | Formula | $CuSO_4 \cdot 5H_2O$ (reference) | Powder 1 | Powder 8 | Powder 4 |
|---|---|---|---|---|---|
| Calcite | $CaCO_3$ | — | 98.3 | 84.7 | 96.1 |
| Gypsum | $CaSO_4 \cdot 2H_2O$ | — | 0.2 | 7.8 | 1.4 |
| Chalcanthite | $CuSO_4 \cdot 5H_2O$ | 100 | — | — | — |
| Brochantite | $Cu_4SO_4(OH)_6$ | — | <0.1 | 2.0 | 0.8 |
| Malachite | $Cu_2CO_3(OH)_2$ | — | 0.9 | 5.5 | 1.0 |
| other constituents | — | — | <0.6 | <0.2 | 0.6 |
| Total |  |  | 100 | 100 | 100 |

Data were normalized to 100% crystalline material.

TABLE 5b

Quantitative Rietveld analyses (XRD) of the powders 12, 14, and 15.

| Mineral | Formula | Powder 12 | Powder 14 | Powder 15 |
|---|---|---|---|---|
| Calcite | $CaCO_3$ | 89.4 | 84.5 | 80.1 |
| Gypsum | $CaSO_4 \cdot 2H_2O$ | — | 7.7 | 7.6 |
| Chalcanthite | $CuSO_4 \cdot 5H_2O$ | — | — | — |
| Brochantite | $Cu_4SO_4(OH)_6$ | — | — | 3.1 |
| Malachite | $Cu_2CO_3(OH)_2$ | 9.0 | 6.7 | 2.4 |
| other constituents | — | 1.6 | 1.1 | 6.8 |
| Total |  | 100 | 100 | 100 |

Data were normalized to 100% crystalline material.

4. Slurries of Modified Mineral-Based Filler and Paper Coating

Examples 20 to 37 (E20-E37) and Comparative Examples 5-12 (CE5 to 12)

Slurries were prepared on a Pendraulik stirrer, by stirring mixtures of the compositions indicated in Table 6 below for 10 minutes at room temperature with 930 rpm.

TABLE 6

Composition of produced filler slurries.

| Example | Powder | Powder [parts] | Water [parts] | DA [parts] | Solid content [wt.-%] | Brookfield viscosity [m · Pas] | pH | Conductivity [mS/cm] |
|---|---|---|---|---|---|---|---|---|
| CE5 | C1 | 100 | 50 | 0.23 | 66.8 | 62 | 10.0 | 0.97 |
| CE6 | C3 | 100 | 50 | 0.23 | 66.2 | 211 | 10.2 | 1.10 |
| CE7 | C4 | 100 | 50 | 0.23 | 66.5 | 208 | 10.1 | 1.12 |
| E20 | 1 | 100 | 62.5 | 0.32 | 61.2 | 786 | 9.0 | 3.18 |
| E21 | 2 | 100 | 50 | 0.23 | 66.1 | 530 | 8.4 | 2.13 |
| E22 | 3 | 100 | 50 | 0.23 | 65.4 | 76.2 | 9.5 | 1.48 |
| E23 | 4 | 100 | 75 | 0.23 | 56.5 | 154 | 8.4 | 2.35 |
| E24 | 5 | 100 | 60 | 0.23 | 61.5 | 53.2 | 9.9 | 1.25 |
| E25 | 9 | 100 | 50 | 0.23 | 66.1 | 526 | 8.6 | 2.22 |
| E26 | 10 | 100 | 50 | 0.23 | 66.4 | 62.4 | 9.7 | 1.23 |
| E27 | 11 | 100 | 50 | 0.23 | 66.1 | 64.4 | 9.9 | 1.21 |
| E28 | 13 | 100 | 50 | 0.23 | — | 661 | 8.4 | 2.74 |

DA = dispersing agent (100% sodium-neutralised polyacrylate, $M_w$ = 3 500 g/mol, pH = 8).

Coating colours containing 100 parts of $CaCO_3$ (w/w) and 6 parts (dry/dry) of Styronal D628 (BASF, Germany) were then prepared with slurries according to Examples 20 to 28 and Comparative Examples 5, 6 and 7 and coated on superYUPO® foils from Fischer Papier AG, Switzerland (thickness 80 μm, size: 18×26 cm, 62 g/m², polypropylene). The composition of the coating colours and coating weights are summarized in Table 7 below.

TABLE 7

Coating colour preparation and coating weight.

| Example | Slurry | Coating colour composition | | | Coating weight [g/m²] |
|---|---|---|---|---|---|
| | | $CaCO_3$ [parts] | Styronal D628 [parts, dry/dry] | Solid content [wt.-%] | |
| CE8 | CE5 | 100 | 6 | 60 | 29.7 |
| CE9 | CE6 | 100 | 6 | 60 | 22.5 |
| CE10 | CE7 | 100 | 6 | 60 | 23.0 |
| CE11[a] | CE6 | 100[b] | 6 | 60 | 22.4 |
| CE12[a] | CE6 | 100[c] | 6 | 60 | 22.3 |
| E29 | E20 | 100 | 6 | 60 | 25.6 |
| E30 | E21 | 100 | 6 | 60 | 26.0 |
| E31 | E22 | 100 | 6 | 60 | 22.3 |
| E32 | E23 | 100 | 6 | 55 | 22.9 |
| E33 | E24 | 100 | 6 | 60 | 26.1 |
| E34 | E25 | 100 | 6 | 60 | 22.0 |
| E35 | E26 | 100 | 6 | 60 | 23.2 |
| E36 | E27 | 100 | 6 | 60 | 23.1 |
| E37 | E28 | 100 | 6 | 60 | 22.7 |

[a]0.23 parts of 100 sodium-neutralised polyacrylates ($M_w$ = 3 500 g/mol, pH = 8) added as dispersing agent;
[b]untreated calcium carbonate but blended with 0.05 parts basic copper(ii)carbonate (powder available from Sigma Aldrich, Germany);
[c]untreated calcium carbonate but blended with 0.02 parts basic copper(ii)carbonate (powder available from Sigma Aldrich, Germany);

5. Polymers Containing Modified Mineral-Based Fillers

Examples 38 and 39 (E38 and E39) and Comparative Example 12 (CE12)

Filled polymer sample have been produced in two steps:

In a first step, the filler and the polymer (ExxonMobil LLDPE 1001, ExxonMobile Chemical, USA) were compounded on a roll mill (Collin 150, Walzwerk 150×400, Germany) with 125 g of material (80:20 polymer and carbonate) using the conditions given in Table 8 below.

TABLE 8

Compounding conditions.

| Composition | $CaCO_3$ powder | 25 g |
|---|---|---|
| | Exxon Mobil plastic 1001 (LLDPE Low density polyethylene) | 100 g |
| Roll speed | 20 upm | |
| Speed difference (typical) | −35% | |
| Thickness: | 0.7/0.8 mm | |
| Temperature | 180° C. | |

LLDPE was injected first, followed by the $CaCO_3$ powder once the LLDPE had melted. Once a homogeneous mixture was obtained, the melt was removed from the rolls and added again (operation repeated 5 times).

Once removed from the rolls, the foils were treated in a second step in a Press (Collin P 300 P, Dr. Collin, Germany). 62 g of polymer were cut in pieces and pressed between 2 metal plates to obtain sheets of the following dimensions: 169×169×2 mm³. The used press program is summarised in Table 9.

TABLE 9

Press conditions.

| Temperature [° C.] | Time [s] | Pressure [bar] |
|---|---|---|
| 190 | 120 | 20 |
| 190 | 60 | 200 |
| cooling | 60 | 200 |

TABLE 10

Summary of samples and compositions.

| Example | Powder | $CuSO_4$ in powder [parts per 100 parts $CaCO_3$] | Powder [g] | LLDPE [g] |
|---|---|---|---|---|
| CE12 | C2 | 0 | 25 | 100 |
| E39 | 6 | 1 | 25 | 100 |
| E40 | 7 | 1 | 25 | 100 |

The surface of the obtained polymer sheets was flat and homogenous.

6. Preparation of Paint Coating Samples

The paint formulations have been prepared according to the methods known to the skilled person ("European Coatings Handbook" Dr. Thomas Brock/Dr. Michael Groteklaes/Dr. Peter Mischke, Curt R. Vincentz Verlag, Hannover, ISBN 3-87870-559-X).

For Indoor paint formulation, the following ingredients were combined in the stated order and amounts.

260 g deionised water, 1 g Calgon N Neu (ICL Performance Products, Tel-Aviv, Israel), 5 g Bermocoll Prime 3500 (Akzo Nobel, Amsterdam, Netherlands), 1 g 10 wt.-% sodium hydroxide (CAS NO. 1310-73-2), 3 g Byk 038 (Byk, Wesel, Germany), 3 g Ecodis P50 (Coatex, Genay, France), 100 g TiONA 595 (Cristal Global, Jeddah, Saudi Arabia), 30 g Optiwhite (Burgess Pigment, Sandersville, Ga. USA), 80 g Omyacarb Extra-CL (Omya International AG, Oftringen, Switzerland), 80 g Omya-Calcimatt-AV (Omya International AG, Oftringen, Switzerland), 165 g modified mineral-based filler or corresponding untreated mineral, 2 g Byk 038 (Byk, Wesel, Germany), 120 g Mowilith LDM 1871 53 wt.-% solid content (Celanese, Irving, Tex. USA), 68 g deionised water.

For outdoor paint formulation, the following ingredients were combined in the stated order and amounts.

150 g deionised water, 3 g Bermocoll EHM 200 (Akzo Nobel, Amsterdam, Netherlands), 2 g 24 wt.-% ammonia (CAS NO. 7664-41-7), 3 g Coapur 2025 (Coatex, Genay, France), 1 g Calgon N Neu (ICL Performance Products, Tel-Aviv, Israel), 5 g Borchigen DFN (OMG Borchers GmbH, Langenfeld, Germany), 10 g Di(propylene glycol) butyl ether (CAS NO. 29911-28-2), 10 g Texanol (Eastman Chemical Company, Kingsport, Tenn., United States), 3 g Byk 038 (Byk, Wesel, Germany), 200 g TiONA 595 (Cristal Global, Jeddah, Saudi Arabia), 20 g Alusil ET (PQ Corporation, Malvern, Pa., United States), 70 g Finntalc M20SL (Mondo Minerals, Amsterdam, Netherlands), 140 g modified mineral-based filler or corresponding untreated mineral, 2 g Byk 038 (Byk, Wesel, Germany), 330 g Mowilith LDM 7717, 46 wt.-% solid content (Celanese, Irving, Tex. USA), 50 g deionised water.

7. Antimicrobial Activity Tests

Example 41—Antimicrobial Activity of Paper Coatings

The antimicrobial activity of selected paper samples comprising a coating layer containing the modified mineral-based filler of the present invention, which were prepared according to Examples E29 to E36, was tested as described in the measurement method section above.

Tables 11 and 12 show the cfu counts per test item and the calculated antimicrobial activity against *S. aureus* (Table 11) and *E. coli* (Table 12) of the coated paper samples E29 to E36 as well as of comparative samples CE8 to CE12 (untreated test items and blends). The term LOD in Tables 11 and 12 refers to the limit of detection.

TABLE 11

Antimicrobial activity against *S. aureus* of surface coated paper samples.

| Test item | Set | cfu/test item | | | | Antimicrobial activity | |
| | | I | II | III | Average | R | LOD |
| --- | --- | --- | --- | --- | --- | --- | --- |
| untreated test item CE8 (before incubation) | 1 | 2.0E+05 | 2.0E+05 | 2.1E+05 | 2.0E+05 | N/A | N/A |
| untreated test item CE8 | 1 | 1.3E+05 | 1.8E+05 | 1.7E+05 | 1.6E+05 | 0.00 | 4.21 |
| Paper from E31 | 1 | 1.0E+01 | 1.0E+01 | 1.0E+01 | 1.0E+01 | 4.21 | 4.21 |
| Paper from E33 | 1 | 1.0E+01 | 1.0E+01 | 1.0E+01 | 1.0E+01 | 4.21 | 4.21 |
| Paper from E30 | 1 | 1.0E+01 | 1.0E+01 | 1.0E+01 | 1.0E+01 | 4.21 | 4.21 |
| untreated test item CE8 (before incubation) | 2 | 1.5E+05 | 1.4E+05 | 1.2E+05 | 1.4E+05 | N/A | N/A |
| untreated test item CE8 | 2 | 8.8E+04 | 1.0E+05 | 8.3E+04 | 9.1E+04 | 0.00 | 3.96 |
| Paper from E30 | 2 | 1.0E+01 | 1.0E+01 | 1.0E+01 | 1.0E+01 | 3.96 | 3.96 |
| Paper from E29 | 2 | 1.0E+01 | 1.0E+01 | 1.0E+01 | 1.0E+01 | 3.96 | 3.96 |
| Untreated test item CE8 (before incubation) | 3 | 1.6E+05 | | | 1.6E+05 | | |
| untreated test item CE8 | 3 | 1.1E+05 | | | 1.1E+05 | 0.00 | 4.05 |
| Paper from E31 | 3 | 1.0E+01 | | | 1.0E+01 | 4.05 | 4.05 |
| Paper from E33 | 3 | 1.5E+01 | | | 1.5E+01 | 3.87 | 4.05 |
| Paper from E30 | 3 | 1.0E+01 | | | 1.0E+01 | 4.05 | 4.05 |
| untreated test item CE8 (before incubation) | 4 | 1.3E+05 | | | 1.3E+05 | N/A | N/A |
| untreated test item CE8 | 4 | 7.0E+04 | | | 7.0E+04 | 0.00 | 3.85 |
| Paper from E30 | 4 | 1.0E+01 | | | 1.0E+01 | 3.85 | 3.85 |
| Paper from E29 | 4 | 1.0E+01 | | | 1.0E+01 | 3.85 | 3.85 |
| untreated test item CE9 (before incubation) | 5 | 1.9E+05 | 1.8E+05 | 1.9E+05 | 1.9E+05 | N/A | N/A |
| untreated test item CE9 | 5 | 2.6E+05 | 2.1E+05 | 2.1E+05 | 2.3E+05 | 0.00 | 4.35 |
| Paper from E34 | 5 | 1.0E+01 | 1.0E+01 | 1.2E+01 | 4.5E+01 | 3.70 | 4.35 |
| Paper from E35 | 5 | 1.0E+01 | 1.0E+01 | 1.0E+01 | 1.0E+01 | 4.35 | 4.35 |
| untreated test item (CE9) (before incubation) | 1 | 1.3E+05 | 1.3E+05 | 1.3E+05 | 1.3E+05 | N/A | N/A |
| untreated test item (CE9) | 1 | 2.0E+05 | 2.1E+05 | 1.5E+05 | 1.8E+05 | 0.00 | 4.26 |
| Paper from E35 | 1 | 1.0E+01 | 1.0E+01 | 1.0E+01 | 1.0E+01 | 4.26 | 4.26 |
| Paper from E36 | 1 | 2.0E+01 | 1.0E+01 | 2.5E+01 | 1.8E+01 | 4.00 | 4.26 |
| Paper from CE11 | 1 | 1.2E+03 | 9.5E+02 | 1.0E+02 | 7.5E+02 | 2.39 | 4.26 |
| Paper from CE12 | 1 | 1.5E+05 | 1.3E+05 | 8.8E+04 | 1.2E+05 | 0.18 | 4.26 |

N/A: Not applicable, results from four independent sets of experiments are shown, each set with its own untreated test items as control. For each test item, experiments were performed once in triplicates and once using a single test item.

TABLE 12

Antimicrobial activity against E. coli of surface coated paper samples.

| Test item | Set | cfu/test item | | | | Antimicrobial activity | |
| --- | --- | --- | --- | --- | --- | --- | --- |
| | | I | II | III | Average | R | LOD |
| untreated test item CE8 (preincubation) | 1 | 3.2E+05 | 3.4E+05 | 3.3E+05 | 3.3E+05 | N/A | N/A |
| untreated test item CE8 | 1 | 2.6E+07 | 2.5E+07 | 2.7E+07 | 2.6E+07 | 0.00 | 6.41 |
| Paper from E31 | 1 | 5.4E+02 | 1.0E+01 | 1.0E+01 | 1.9E+02 | 5.14 | 6.41 |
| Paper from E33 | 1 | 1.0E+01 | 1.0E+01 | 1.0E+01 | 1.0E+01 | 6.41 | 6.41 |
| Paper from E30 | 1 | 1.0E+01 | 1.0E+01 | 1.0E+01 | 1.0E+01 | 6.41 | 6.41 |
| untreated test item CE8 (preincubation) | 2 | 3.6E+05 | 3.7E+05 | 3.6E+05 | 3.6E+05 | N/A | N/A |
| untreated test item CE8 | 2 | 4.2E+06 | 4.4E+06 | 9.4E+06 | 6.0E+06 | 0.00 | 5.78 |
| Paper from E30 | 2 | 1.0E+01 | 1.0E+01 | 1.0E+01 | 1.0E+01 | 5.78 | 5.78 |
| Paper from E29 | 2 | 3.5E+01 | 1.0E+01 | 1.0E+01 | 1.8E+01 | 5.51 | 5.78 |

N/A: Not applicable; results from two independent sets of experiment are shown, each set with its own untreated test items as control.

Example 42—Fungal Growth Resistance of Paper Coatings

The antifungal activity of selected paper samples comprising a coating layer containing the modified mineral-based filler of the present invention, which were prepared according to Examples E18 to E22, was tested as described in the measurement method section above.

Tables 13a to 13d below show the rating of fungal defacement for each test item.

TABLE 13a

Fungal defacement of different surface coated paper samples by *Aspergillus niger* (ATCC 6275) in a fungal growth resistant test after 19 days incubation at 28° C. and 90% relative humidity performed in two different sets.

| Test item | Set | Rating[1] | % defacement[1] |
| --- | --- | --- | --- |
| untreated test item CE8 | 1 | 4 | 51% to 60% |
| Paper from E29 | 1 | 10 | 0% |
| Paper from E32 | 1 | 10 | 0% |
| untreated test item CE8 | 2 | 5 | 41% to 50% |
| Paper from E33 | 2 | 10 | 0% |
| Paper from E30 | 2 | 8 | 11% to 20% |

[1]According to ASTM D3273-D12; N/A: Not applicable.

TABLE 13b

Fungal defacement of different surface coated paper samples by *Aspergillus niger* (ATCC 6275) in a fungal growth resistant test after 32 days incubation at 28° C. and 90% relative humidity performed in triplicates.

| Test item | Rating[1] | Average Rating[1] | Average % defacement[1] |
| --- | --- | --- | --- |
| untreated test item CE8 | 2, 2, 2 | 2 | 80% |
| Paper from E29 | 9, 9, 9 | 9 | 10% |
| Paper from E30 | 9, 9, 8 | 8.7 | 13% |
| Paper from E31 | 8, 8, 8 | 8 | 20% |
| Paper from E32 | 9, 9, 9 | 9 | 10% |
| Paper from E33 | 9, 9, 9 | 9 | 10% |

[1]According to ASTM D3273-D12, average from triplicates.

TABLE 13c

Fungal defacement of different surface coated paper samples by *Aureobasidium pullans* (ATCC 9348) in a fungal growth resistant test after 32 days incubation at 28° C. and 90% relative humidity performed in triplicates.

| Test item | Rating[1] | Average Rating[1] | Average % defacement[1] |
| --- | --- | --- | --- |
| untreated test item CE8 | 9, 9, 9 | 9 | 10% |
| Paper from E29 | 10, 10, 9 | 9.7 | 3% |
| Paper from E30 | 10, 10, 10 | 10 | 0% |
| Paper from E31 | 10, 10, 9 | 9.7 | 3% |
| Paper from E32 | 10, 10, 10 | 10 | 0% |
| Paper from E33 | 10, 10, 10 | 10 | 0% |

[1]According to ASTM D3273-D12, average from triplicates.

TABLE 13d

Fungal defacement of different surface coated paper samples by *Penicillium funiculosum* (ATCC 11797) in a fungal growth resistant test after 32 days incubation at 28° C. and 90% relative humidity performed in triplicates.

| Test item | Rating[1] | Average Rating[1] | Average % defacement[1] |
| --- | --- | --- | --- |
| untreated test item CE8 | 8, 6, 6 | 6.7 | 33% |
| Paper from E29 | 10, 9, 9 | 9.3 | 7% |
| Paper from E30 | 10, 10, 9 | 9.7 | 3% |
| Paper from E31 | 10, 10, 10 | 10 | 0% |
| Paper from E32 | 9, 9, 9 | 9 | 10% |
| Paper from E33 | 10, 10, 10 | 10 | 0% |

[1]According to ASTM D3273-D12, average from triplicates.

Example 43—Antimicrobial Surface Activity of Polymers

The antimicrobial activity of selected polymer samples the modified mineral-based filler of the present invention, which were prepared according to Example E40, was tested as described in the measurement method section above.

Table 14 shows the cfu counts per test item and the calculated antimicrobial activity against *S. aureus* of polymers containing modified mineral-based fillers of the present invention Results from two independent sets of experiment are shown, each set with its own untreated test items (CE13) as control. For each test item, experiments were performed once in triplicates and once using a single test item.

TABLE 14

Antimicrobial activity against *S. aureus* in a polymers containing modified mineral based fillers.

| Test item | Set | cfu/test item | | | | Antimicrobial activity | |
|---|---|---|---|---|---|---|---|
| | | I | II | III | Average | R | LOD |
| untreated test item CE13 (before incubation) | 1 | 1.8E+05 | 1.8E+05 | 1.8E+05 | 1.8E+05 | N/A | N/A |
| untreated test item CE13 | 1 | 2.2E+05 | 1.5E+05 | 1.7E+05 | 1.8E+05 | 0.00 | 4.26 |
| Polymer from E40 | 1 | 6.9E+04 | 5.6E+04 | 3.5E+03 | 4.3E+04 | 0.63* | 4.26 |
| untreated test item CE13 (before incubation) | 2 | 1.6E+05 | | | 1.6E+05 | | |
| untreated test item CE13 | 2 | 2.8E+04 | | | 2.8E+04 | 0.00 | 3.44 |
| Polymer from E40 | 2 | 2.4E+03 | | | 2.4E+03 | 1.06 | 3.44 |

N/A: Not applicable;
LOD: Limit of Detection;
*Statistical significant difference compared to untreated test item (p < 0.05, t-test two tailed, homoscedastic).

The following paint coating samples were prepared. The formulations were spread onto a black reinforced foil (PVC) with 0.15 mm thickness and dried for at least 1 week.

CE14: Indoor paint formulation using untreated calcium carbonate (CE1) as untreated mineral.

E44: Indoor paint formulation using powder 14 as modified mineral-based filler.

E45: Indoor paint formulation using powder 17 as modified mineral-based filler.

E46: Indoor paint formulation using powder 16 as modified mineral-based filler.

CE15: Outdoor paint formulation using untreated calcium carbonate (calcium carbonate from Austria, $d_{50}$=7.1 nm, BET=2.2 m$^2$/g) untreated mineral.

E47: Outdoor paint formulation using powder 19 as modified mineral-based filler.

E48: Outdoor paint formulation using powder 18 as modified mineral-based filler.

E49: Outdoor paint formulation using powder 15 as modified mineral-based filler.

Example 50—Antimicrobial Activity of Paint Coatings Containing Modified Mineral-Based Filler The antimicrobial activities of paint coating samples containing modified mineral-based filler of the present invention, were tested as described in the measurement method section above.

Tables 15 shows the cfu counts per test item and the calculated antimicrobial activity against *S. aureus* (Table 15) of the indicated paint coating samples as well as of comparative samples (untreated test items). The term LOD in Tables 15 refers to the limit of detection.

TABLE 15

Antimicrobial activity against *S. aureus* of paint formulations containing modified mineral-based filler.

| Test item | cfu/test item | | | | Antimicrobial activity | |
|---|---|---|---|---|---|---|
| | I | II | III | Average | R | LOD |
| untreated test item CE15 (before incubation) | 2.7E+05 | 2.6E+05 | 2.6E+05 | 2.6E+05 | N/A | N/A |
| untreated test item CE15 | 5.0E+04 | 5.5E+04 | 4.0E+04 | 4.8E+04 | 0.00 | 3.68 |
| E48 | 1.0E+01 | 2.0E+01 | 1.0E+01 | 1.3E+01 | 3.55 | 3.68 |
| E47 | 1.0E+01 | 1.0E+01 | 1.0E+01 | 1.0E+01 | 3.68 | 3.68 |
| E49 | 1.0E+01 | 1.0E+01 | 1.0E+01 | 1.0E+01 | 3.68 | 3.68 |
| untreated test item CE14 (before incubation) | 2.3E+05 | 2.4E+05 | 2.5E+05 | 2.4E+05 | N/A | N/A |
| untreated test item CE14 | 1.2E+04 | 3.5E+03 | 4.5E+03 | 6.5E+03 | 0.00 | 2.81 |
| E46 | 1.0E+01 | 1.0E+01 | 1.0E+01 | 1.0E+01 | 2.81 | 2.81 |
| E45 | 1.0E+01 | 1.0E+01 | 1.0E+01 | 1.0E+01 | 2.81 | 2.81 |
| E44 | 1.0E+01 | 1.0E+01 | 1.0E+01 | 1.0E+01 | 2.81 | 2.81 |

Example 51—Antialgal Activity of Modified Mineral-Based Filler

The antialgal efficacy of various types of coatings containing modified mineral-based filler of the present invention, which were prepared according to Examples E33 and E29 was determined according to the test norm described above. Table 16 shows the results of the test.

TABLE 16

Antimicrobial activity against the green algae *Stichococcus bacillaris* of coatings containing modified mineral-based filler.

| Test item | Rating of triplicates at different time points | | | |
|---|---|---|---|---|
| | Day 14 | Day 21 | Day 28 | Day 32 |
| untreated test item* (Paper from CE8) | 2, 2, 2 | 2, 2, 2 | 2, 2, 2 | 2, 2, 2 |
| Paper from E33 | 1, 1, 1 | 1, 1, 1 | 1, 1, 1 | 1, 1, 1 |
| Paper from E29 | 1, 1, 2 | 2, 1, 1 | 1, 1, 1 | 1, 1, 1 |

The rating of the untreated test item is by definition 2.

Results

Example 41 shows the antimicrobial surface activity of dried paper coatings against gram positive bacteria (*S. aureus*) and gram negative bacteria (*E. coli*). All test samples containing the inventive modified mineral based filler (papers E29 to E36) showed a very strong antimicrobial activity. In almost any case, the antimicrobial activity reaches and most likely exceeds the limit of detection of the test assay. This antimicrobial surface activity is also apparent in polymers containing the inventive modified mineral-based filler (Example 43). The activity though is lower in polymers than on the paper coatings which are filled to a higher degree with the inventive modified mineral-based filler than the polymers.

Example 42 exemplifies the antimicrobial surface activity of dried paper coatings against fungal defacement under humid conditions due to microbial activity of three different fungi (*Aspergillus niger* ATCC 6275, *Aureobasidium pullulans* ATCC 9348, *Penicillium funiculosum* ATCC 11797). All test samples containing the inventive modified mineral based filler (Papers E29 to E36) showed a reduced or even absent defacement of the coating compared to the sample containing untreated calcium carbonate (paper from CE8) (see Tables 13a-d).

The invention claimed is:

1. A process for manufacturing a modified mineral-based filler with antimicrobial activity comprising the following steps:
   (i) providing at least one alkaline earth metal carbonate-comprising material, wherein said alkaline earth metal carbonate-comprising material is ground calcium carbonate or dolomite, or mixtures thereof,
   (ii) providing at least one water soluble copper salt selected from copper nitrate, copper sulphate, copper acetate, copper chloride, copper bromide, hydrates thereof, and any mixture thereof, and wherein the at least one water soluble copper salt is added in an amount from 0.01 to 3 wt.-%, based on the total weight of the at least one alkaline earth carbonate-comprising material,
   (iii) contacting the at least one alkaline earth metal carbonate-comprising material of step (i), the at least one water soluble copper salt of step (ii), and optionally water, in one or several steps to form a mixture,
   (iv) heating the mixture obtained from step (iii) to a temperature in the range from 70 to 140° C.,
   (v) optionally separating the modified mineral-based filler from an aqueous suspension obtained from step (iv), and
   (vi) drying until the moisture content of the modified mineral-based filler is less than or equal to 1.0 wt.-%, based on the total weight of the dried modified mineral-based filler.

2. The process according to claim 1, wherein the process is a batch process or a continuous process.

3. The process according to claim 1, wherein the mixture formed in step (iii) is an aqueous suspension, and the process comprises step (v).

4. The process according to claim 1, wherein step (vi) is performed at a temperature in the range from 60 to 200° C.

5. The process according to claim 4, wherein the modified mineral-based filler is dried to a moisture content of between 0.01 and 0.15 wt.-%, based on the total weight of the dried modified mineral-based filler.

6. The process according to claim 3, wherein step (vi) is performed at a temperature in the range from 60 to 200° C.

7. The process according to claim 6, wherein the modified mineral-based filler is dried to a moisture content of between 0.01 and 0.15 wt.-%, based on the total weight of the dried modified mineral-based filler.

8. The process according to claim 1, wherein the process further comprises a step of treating the modified mineral-based filler obtained in step (iv) during and/or after step (iv) in one or more steps with at least one hydrophobising agent at a temperature from 30 to 200° C., wherein the at least one hydrophobising agent is added in an amount such that the total weight of the at least one hydrophobising agent on the total surface area of the modified mineral-based filler is from 0.001 to 10 mg/m$^2$.

9. The process according to claim 1, wherein the at least one water soluble copper salt of step (ii) is provided in a form of an aqueous solution or aqueous suspension.

10. The process according to claim 1, wherein the at least one water soluble copper salt of step (ii) is provided in a form of an aqueous solution or aqueous suspension comprising carbonate ions, wherein the carbonate ions are derived from a carbonate-comprising compound, which is dissolved in the aqueous solution or aqueous suspension of the at least one water soluble copper salt, or are generated in-situ by treating the aqueous solution or aqueous suspension of the at least one water soluble copper salt with gaseous carbon dioxide.

11. The process according to claim 1, wherein the at least one alkaline earth metal carbonate-comprising material of step (i) is provided in a form of an aqueous suspension.

12. The process according to claim 1, wherein the at least one alkaline earth metal carbonate-comprising material of step (i) is provided in form of an aqueous suspension comprising carbonate ions, wherein the carbonate ions are at least partially derived from a carbonate-comprising compound, which differs from the at least one alkaline earth metal carbonate-comprising material of step (i) and is dissolved in the aqueous suspension, or are generated in-situ by treating the aqueous suspension of the at least one alkaline earth metal carbonate-comprising material with gaseous carbon dioxide.

13. The process according to claim 1, wherein the at least one alkaline earth metal carbonate-comprising material is selected from the group consisting of dolomitic marble, magnesitic marble, limestone, chalk, and any mixture thereof.

14. The process according to claim 1, wherein the at least one alkaline earth metal carbonate-comprising material is ground calcium carbonate.

15. The process according to claim 1, wherein the at least one water soluble copper salt is copper sulphate, hydrates thereof, and mixtures thereof.

16. The process according to claim 1, wherein the process further comprises a step of grinding and/or fractionating and/or classifying the mixture obtained from step (iii) before, during or after step (iv).

17. The process according to claim 3, wherein the process further comprises a step of treating the modified mineral-based filler that has been separated from an aqueous suspension, with at least one hydrophobising agent at a temperature from 30 to 200° C., wherein the at least one hydrophobising agent is added in an amount such that the total weight of the at least one hydrophobising agent on the total surface area of the modified mineral-based filler is from 0.001 to 10 mg/m$^2$.

18. The process according to claim 4, wherein the process further comprises a step of treating modified mineral-based filler that has been dried, with at least one hydrophobising agent at a temperature from 30 to 200° C., wherein the at least one hydrophobising agent is added in an amount such that the total weight of the at least one hydrophobising agent on the total surface area of the modified mineral-based filler is from 0.001 to 10 mg/m$^2$.

19. The process according to claim 5, wherein the modified mineral-based filler is dried to a moisture content of between 0.02 and 0.10 wt.-%, based on the total weight of the dried modified mineral-based filler.

20. The process according to claim 19, wherein the modified mineral-based filler is dried to a moisture content of between 0.03 and 0.07 wt.-%, based on the total weight of the dried modified mineral-based filler.

21. The process according to claim 7, wherein the modified mineral-based filler is dried to a moisture content of between 0.02 and 0.10 wt.-%, based on the total weight of the dried modified mineral-based filler.

22. The process according to claim 21, wherein the modified mineral-based filler is dried to a moisture content of between 0.03 and 0.07 wt.-%, based on the total weight of the dried modified mineral-based filler.

23. The process according to claim 4, wherein the modified mineral-based filler is dried to a moisture content of less than or equal to 0.2 wt.-%, based on the total weight of the dried modified mineral-based filler.

24. The process according to claim 6, wherein the modified mineral-based filler is dried to a moisture content of less than or equal to 0.2 wt.-%, based on the total weight of the dried modified mineral-based filler.

* * * * *